United States Patent
Barron et al.

(10) Patent No.: US 12,208,279 B2
(45) Date of Patent: Jan. 28, 2025

(54) LIGHT THERAPY AS AN ADJUVANT TO CAROTID ENDARTERECTOMY

(71) Applicant: Reversal Solutions, Inc., Belmont, CA (US)

(72) Inventors: Annelise E. Barron, Redwood City, CA (US); Peter E. Newsome, Woodside, CA (US); John A. Fortkort, Austin, TX (US)

(73) Assignee: Reversal Solutions, Inc., Belmont, CA (US)

( * ) Notice: Subject to any disclaimer, the term of this patent is extended or adjusted under 35 U.S.C. 154(b) by 521 days.

(21) Appl. No.: 17/481,293

(22) Filed: Sep. 21, 2021

(65) Prior Publication Data

US 2022/0088408 A1    Mar. 24, 2022

Related U.S. Application Data

(60) Provisional application No. 63/081,317, filed on Sep. 21, 2020.

(51) Int. Cl.
*A61N 5/06* (2006.01)

(52) U.S. Cl.
CPC .... *A61N 5/0618* (2013.01); *A61N 2005/0632* (2013.01); *A61N 2005/0635* (2013.01); *A61N 2005/0659* (2013.01); *A61N 2005/0663* (2013.01)

(58) Field of Classification Search
CPC .......... A61N 5/0618; A61N 2005/0632; A61N 2005/0635; A61N 2005/0659; A61N 2005/0663; A61N 2005/0643; A61N 5/0613
See application file for complete search history.

(56) References Cited

U.S. PATENT DOCUMENTS

| | | |
|---|---|---|
| 7,354,432 B2 | 4/2008 | Eells et al. |
| 9,814,903 B2 | 11/2017 | Dotson et al. |
| 10,226,563 B2 | 3/2019 | Garrison et al. |
| 10,391,330 B2 | 8/2019 | Bourke et al. |
| 10,537,728 B2 | 1/2020 | Simon et al. |
| 10,596,037 B2 | 3/2020 | Tedford et al. |
| 10,653,889 B2 | 5/2020 | De Taboada et al. |
| 10,788,500 B2 | 9/2020 | Lee |

(Continued)

FOREIGN PATENT DOCUMENTS

| | | | | |
|---|---|---|---|---|
| CN | 107075127 A | * | 8/2017 | .......... A61K 31/785 |
| WO | 2019053625 A1 | | 3/2019 | |

(Continued)

OTHER PUBLICATIONS

"Yamada et al. Photobiomodulation therapy in knee osteoarthritis reduces oxidative stress and inflammatory cytokines in rat, Sep. 12, 2019, Journal of Biophotonics". (Year: 2019).*

(Continued)

*Primary Examiner* — Carl H Layno
*Assistant Examiner* — Aya Ziad Bakkar
(74) *Attorney, Agent, or Firm* — John A. Fortkort; Fortkort & Houston PC

(57) ABSTRACT

A method for treating a subject is provided. The method includes performing surgery on the subject such as, for example, a carotid endarterectomy. Light therapy is administered to the subject as an adjuvant to the surgery.

38 Claims, 19 Drawing Sheets

(56) References Cited

U.S. PATENT DOCUMENTS

| | | |
|---|---|---|
| 10,952,882 B2 | 3/2021 | Cou et al. |
| 2003/0109906 A1 | 6/2003 | Streeter |
| 2005/0182287 A1* | 8/2005 | Becker .................. A61N 2/008 336/122 |
| 2007/0179570 A1 | 8/2007 | De Taboada et al. |
| 2008/0091249 A1 | 4/2008 | Wang |
| 2008/0221211 A1 | 9/2008 | Streeter |
| 2014/0243933 A1 | 8/2014 | Ginggen |
| 2016/0129278 A1 | 5/2016 | Mayer |
| 2019/0001150 A1 | 1/2019 | Toselli et al. |
| 2019/0015679 A1 | 1/2019 | Taboada et al. |
| 2019/0142636 A1 | 5/2019 | Tedford et al. |
| 2019/0175936 A1 | 6/2019 | Gretz et al. |
| 2019/0246463 A1 | 8/2019 | Williams et al. |
| 2021/0275827 A1 | 9/2021 | Barron et al. |
| 2023/0055346 A1 | 2/2023 | Fortkort et al. |

FOREIGN PATENT DOCUMENTS

| | | | |
|---|---|---|---|
| WO | WO-2020089209 A1 * | 5/2020 | |
| WO | WO-2020092729 A1 * | 5/2020 | ............... A61N 1/32 |
| WO | 2022020538 A1 | 1/2022 | |
| WO | 2022036156 A1 | 2/2022 | |

OTHER PUBLICATIONS

Chaves ME, Araújo AR, Piancastelli AC, Pinotti M. Effects of low-power light therapy on wound healing: Laser x Led. An Bras Dermatol. 2014;89(4):616-623. doi:10.1590/abd1806-4841. 20142519.

Agrawal T, Gupta GK, Rai V, Carroll JD, Hamblin MR. Preconditioning with low-level laser (light) therapy: light before the storm. Dose Response. Sep. 22, 2014;12(4):619-49. doi: 10.2203/dose-response.14-032.Agrawal. PMID: 25552961; PMCID: PMC4267453.

Ferraresi C, Kaippert B, Avci P, Huang YY, de Sousa MV, Bagnato VS, Parizotto NA, Hamblin MR. Low-level laser (light) therapy increases mitochondrial membrane potential and ATP synthesis in C2C12 myotubes with a peak response at 3-6 h. Photochem Photobiol. Mar.-Apr. 2015;91(2):411-6. doi: 10.1111/php.12397. Epub Dec. 30, 2014. PMID: 25443662; PMCID: PMC4355185.

De Freitas LF, Hamblin MR. Proposed Mechanisms of Photobiomodulation or Low-Level Light Therapy. IEEE J Sel Top Quantum Electron. 2016;22(3):7000417. doi:10.1109/JSTQE.2016.2561201.

David Martin, "How Can Light Therapy Help With Surgical Recovery", https://lightlounge.life/blog/light-therapy/how-can-light-therapy-help-with-surgical-recovery/; downloaded Sep. 21, 2021.

Alster TS, Wanitphakdeedecha R. Improvement of postfractional laser erythema with light-emitting diode photomodulation. Dermatol Surg. May 2009;35(5):813-5. doi: 10.1111/j.1524-4725.2009.01137.x. Epub Apr. 6, 2009. PMID: 19397672.

LED Light Therapy Treatments Before and After Surgery (Mar. 20, 2019); downloaded from https://www.avenueadvancedskincare.com.au/led-light-therapy-treatments-surgery/ on Sep. 21, 2021.

Hamblin MR. Mechanisms and applications of the anti-inflammatory effects of photobiomodulation. AIMS Biophys. 2017;4(3):337-361. doi: 10.3934/biophy.2017.3.337. Epub May 19, 2017. PMID: 28748217; PMCID: PMC5523874.

Lee, Dong-Jin & Jang, Ha-Young & Moon, Ki-Wook & Lee, Eun-Joo & Yoo, A-Ram & Choi, Woo & Sung, Chang & Kim, Jae & Kim, Dae. (2019). Near-infrared light therapy for recovery of cerebral hypoperfusion induced by bilateral common carotid artery stenosis in mice. 51. 10.1117/12.2526907.

Blivet G, Meunier J, Roman FJ, Touchon J. Neuroprotective effect of a new photobiomodulation technique against Aβ25-35 peptide-induced toxicity in mice: Novel hypothesis for therapeutic approach of Alzheimer's disease suggested. Alzheimers Dement (N Y). 2018;4:54-63. Published Feb. 2, 2018. doi:10.1016/j.trci.2017.12.003.

Prindeze NJ, Ardanuy JG, Carney BC, Moffatt LT, Shupp JW. Photobiomodulation Elicits a Differential Cytokine Response in a Cultured Analogue of Human Skin. Eplasty. Mar. 1, 2019;19:e3. PMID: 30858901; PMCID: PMC6404725.

Yamada EF, Bobinski F, Martins DF, Palandi J, Folmer V, da Silva MD. Photobiomodulation therapy in knee osteoarthritis reduces oxidative stress and inflammatory cytokines in rats. J Biophotonics. Jan. 2020;13(1):e201900204. doi: 10.1002/jbio.201900204. Epub Oct. 15, 2019. PMID: 31568634.

Bo M, Massaia M, Speme S, Cappa G, Strumia K, Cerrato P, Ponzio F, Poli L. Risk of cognitive decline in older patients after carotid endarterectomy: an observational study. J Am Geriatr Soc. Jun. 2006;54(6):932-6. doi: 10.1111/j.1532-5415.2006.00787.x. PMID: 16776788.

Du J, Plas M, Absalom AR, van Leeuwen BL, de Bock GH. The association of preoperative anxiety and depression with neurocognitive disorder following oncological surgery. J Surg Oncol. Mar. 2020;121(4):676-687. doi: 10.1002/ jso.25836. Epub Jan. 12, 2020. PMID: 31930514; PMCID: PMC7064888.

Trelles MA, Allones I. Red light-emitting diode (LED) therapy accelerates wound healing post-blepharoplasty and periocular laser ablative resurfacing. J Cosmet Laser Ther. Apr. 2006;8(1):39-42. doi: 10.1080/14764170600607731. PMID: 16581685.

Danielson M, Wiklund A, Granath F, Blennow K, Mkrtchian S, Nellgård B, Oras J, Jonsson Fagerlund M, Granström A, Schening A, Rasmussen LS, Erlandsson Harris H, Zetterberg H, Ricksten SE, Eriksson LI. Neuroinflammatory markers associate with cognitive decline after major surgery: Findings of an explorative study. Ann Neurol. Mar. 2020;87(3):370-382. doi: 10.1002/ana.25678. Epub Jan. 25, 2020. PMID: 31930549.

Köster M, Martens U, Gruber T. Memory entrainment by visually evoked theta-gamma coupling. Neuroimage. Mar. 2019; 188:181-187. doi: 10.1016/j.neuroimage.2018.12.002. Epub Dec. 5, 2018. PMID: 30529173.

Iaccarino HF, Singer AC, Martorell AJ, Rudenko A, Gao F, Gillingham TZ, Mathys H, Seo J, Kritskiy O, Abdurrob F, Adaikkan C, Canter RG, Rueda R, Brown EN, Boyden ES, Tsai LH. Gamma frequency entrainment attenuates amyloid load and modifies microglia. Nature. Dec. 7, 2016;540(7632):230-235. doi: 10.1038/nature20587. Erratum in: Nature. Oct. 2018;562(7725):E1. PMID: 27929004; PMCID: PMC5656389.

Du J, Plas M, Absalom AR, van Leeuwen BL, de Bock GH. The association of preoperative anxiety and depression with neurocognitive disorder following oncological surgery. J Surg Oncol. Mar. 2020; 121(4):676-687. doi: 10.1002/jso.25836. Epub Jan. 12, 2020. PMID: 31930514; PMCID: PMC7064888.

Bo M, Massaia M, Speme S, Cappa G, Strumia K, Cerrato P, Ponzio F, Poli L. Risk of cognitive decline in older patients after carotid endarterectomy: an observational study. J Am Geriatr Soc. Jun. 2006;54(6):932-6. doi: 10.1111/j.1532-5415.2006.00787.x. PMID: 16776788.

Aceto P, Lai C, De Crescenzo F, Crea MA, Di Franco V, Pellicano GR, Perilli V, Lai S, Papanice D, Sollazzi L. Cognitive decline after carotid endarterectomy: Systematic review and meta-analysis. Eur J Anaesthesiol. Nov. 2020; 37(11):1066-1074. doi: 10.1097/EJA.0000000000001130. PMID: 31860600.

Heyer EJ, DeLaPaz R, Halazun HJ, Rampersad A, Sciacca R, Zurica J, Benvenisty AI, Quest DO, Todd GJ, Lavine S, Solomon RA, Connolly ES Jr. Neuropsychological dysfunction in the absence of structural evidence for cerebral ischemia after uncomplicated carotid endarterectomy. Neurosurgery. Mar. 2006;58(3):474-80; discussion 474-80. doi: 10.1227/01.NEU.0000197123.09972.EA. PMID: 16528187; PMCID: PMC1449740.

* cited by examiner

LIGHT THERAPY AS AN ADJUVANT TO CAROTID ENDARTERECTOMY

CROSS-REFERENCE TO RELATED APPLICATIONS

This application claims the benefit of priority of U.S. Patent Application No. 63/081,317 filed Sep. 21, 2020, having the same inventors and entitled "LIGHT THERAPY AS AN ADJUVANT TO CAROTID ENDARTERECTOMY," which is incorporated herein by reference in its entirety.

FIELD OF THE DISCLOSURE

The present application relates generally to light therapy, and more specifically to the use of light therapy as an adjuvant to carotid endarterectomies and other surgical procedures.

BACKGROUND OF THE DISCLOSURE

Carotid endarterectomy is a medical procedure utilized to remedy the effects of plaque-based arterial occlusion in a carotid artery of a subject. Carotid endarterectomies are often performed to reduce the likelihood of stroke in a patient. For example, the procedure may be recommended for patients exhibiting moderate (50-79%) blockages of a carotid artery, and who are experiencing stroke (or mini-stroke) symptoms or transient ischemic attack (TIA). The procedure may also be recommended for patients exhibiting blockages of 80% or more, even if the patient is asymptomatic.

FIG. 1 depicts a portion of a carotid artery in a human subject 101. As seen therein, the carotid artery 105, which is a major blood vessel to the brain 109, includes a main vessel 113 which splits into an internal branch 103 that supplies blood to the brain, and an external branch 107 that supplies blood to the face and neck.

FIG. 2 depicts a cross-sectional area 2A taken from REGION 2 in FIG. 1 for the carotid artery 105 of a healthy human subject. The carotid artery 105 depicted therein is free from any occlusions, and hence provides an unobstructed flow 111 of blood from the base 113 of the artery and through the internal 103 and external 107 branches.

FIG. 3 depicts a cross-sectional area 2B taken from REGION 2 in FIG. 1 for the carotid artery 105 of a human subject suffering from atherosclerosis. In comparison to FIG. 2, the carotid artery 105 depicted in FIG. 3 has plaque deposits 115 which obstruct the flow 111 of blood from the base 113 of the artery and through the internal 103 and external 107 branches. These deposits 115 typically include fat, cholesterol, calcium, and other substances present in the blood. When such plaque deposits 115 become sufficiently extensive, they result in the disease atherosclerosis.

Two general procedures have been developed in the art for performing carotid endarterectomies. In both procedures, the subject is properly anesthetized or otherwise prepared prior to undergoing the procedure using techniques that are well known to the art.

In the first procedure, which is illustrated in FIGS. 4-8, a subject is presented with an arterial occlusion in the form of one or more plaque deposits 407 in a carotid artery 401 (see FIG. 4, which is a cross-sectional portion of the carotid artery corresponding to REGION 2 in FIG. 1). The plaque deposits 407 are sufficiently extensive such that a carotid endarterectomy is indicated.

As seen in FIG. 5, an incision 405 is created in the carotid artery 401. This incision 405 extends through the adventitia (the outer layer of the artery), the media (the muscular middle layer of the artery) and the intima (the smooth, innermost layer of the artery). The incision 405 is held open with a retractor 409 or other suitable instrument, and the plaque deposits 407 (and commonly the entire inner-most lining of the diseased section of the artery 401) are then manually removed with forceps 413 or other suitable instruments. The incision 405 is then closed with appropriate suturing 411 as shown in FIG. 6. As seen in the cross-section of FIG. 8 taken along PLANE 8-8 of FIG. 6, if successful, the operation results in the restoration of normal, non-occluded blood flow through the affected artery 401.

In the second procedure, which is illustrated in FIGS. 9-14, the subject 501 is presented with an arterial occlusion 507 (see FIG. 10) caused by one or more plaque deposits in a carotid artery 503. The plaque deposits 507 are sufficiently extensive, and occlude the flow path 504 significantly enough, that a carotid endarterectomy is indicated.

As seen in FIG. 11, a catheter 523 is inserted into the occluded artery 503 and is utilized to position a stent 525 near the location of the occlusion. As seen in FIG. 12, the stent 525 is then expanded to effectively widen the artery 503 and prevent it from undergoing stenosis. As seen by comparing the pre- and post-procedure cross-sectional views of FIGS. 13 and 14, respectively, if successful, the operation results in the restoration of normal blood flow through the affected artery.

BRIEF DESCRIPTION OF THE DRAWINGS

FIG. 4 depicts the occluded artery. As seen in FIG. 5, an incision is created in the arterial wall and the plaque deposit is physically removed. As seen in FIG. 6, the incision in the cleared artery is then sutured. FIGS. 7 and 8 show the artery before and after the procedure, respectively.

FIGS. 13 and 14 show the artery before and after the procedure, respectively.

FIG. 8(a) depicts brainwaves from the delta band. FIG. 8(b) depicts brainwaves from the theta band. FIG. 8(c) depicts brainwaves from the alpha band. FIG. 8(d) depicts brainwaves from the mu-rhythm band. FIG. 8(e) depicts brainwaves from the beta band. FIG. 8(f) depicts brainwaves from the gamma band.

SUMMARY OF THE DISCLOSURE

Figure 1:
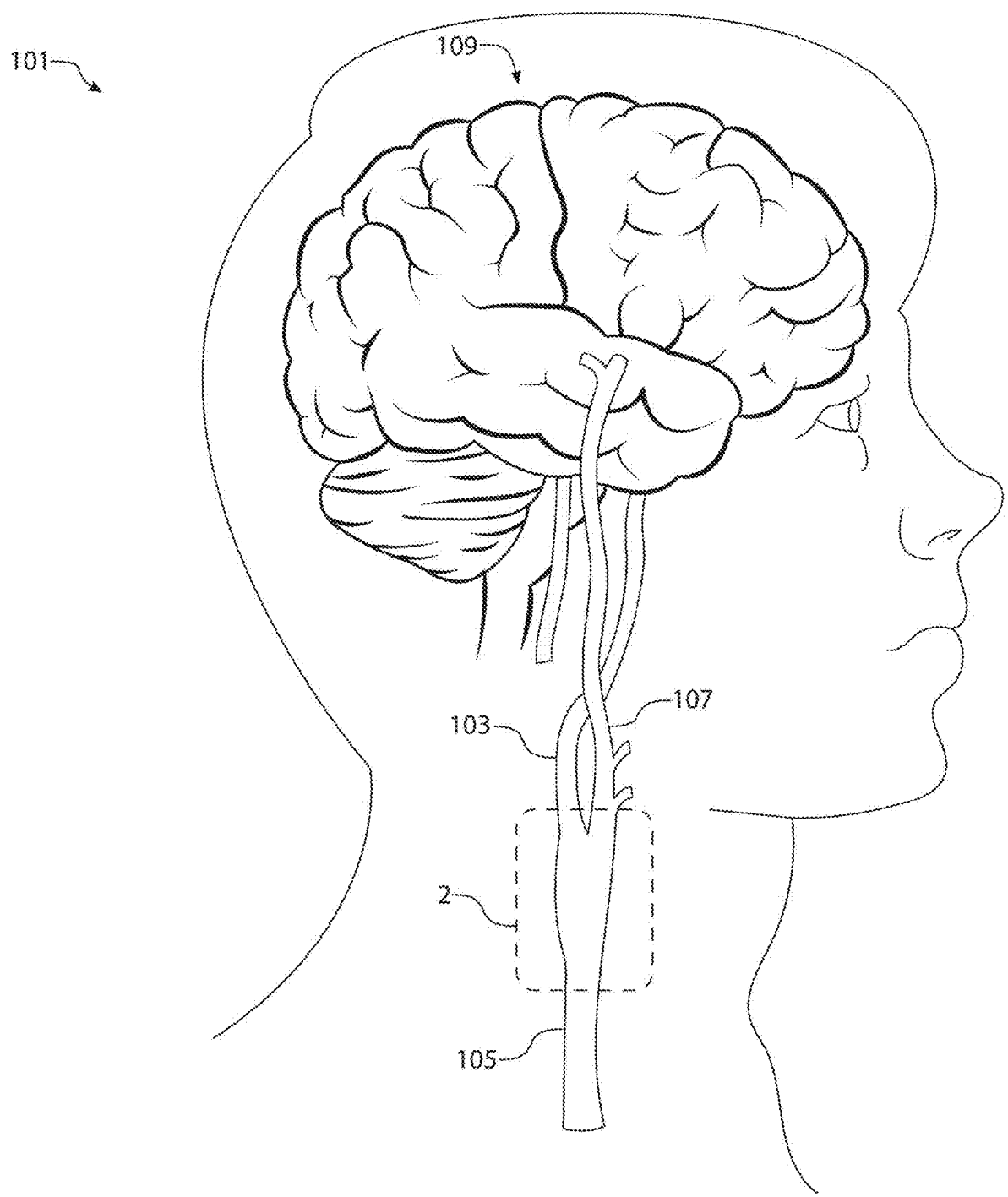
FIG. 1 is an illustration of a carotid artery in a subject, in which some elements of the physiology of the subject have been rendered transparent for purposes of illustration to show the location of the right carotid artery in the neck of a subject.
Figure 2:
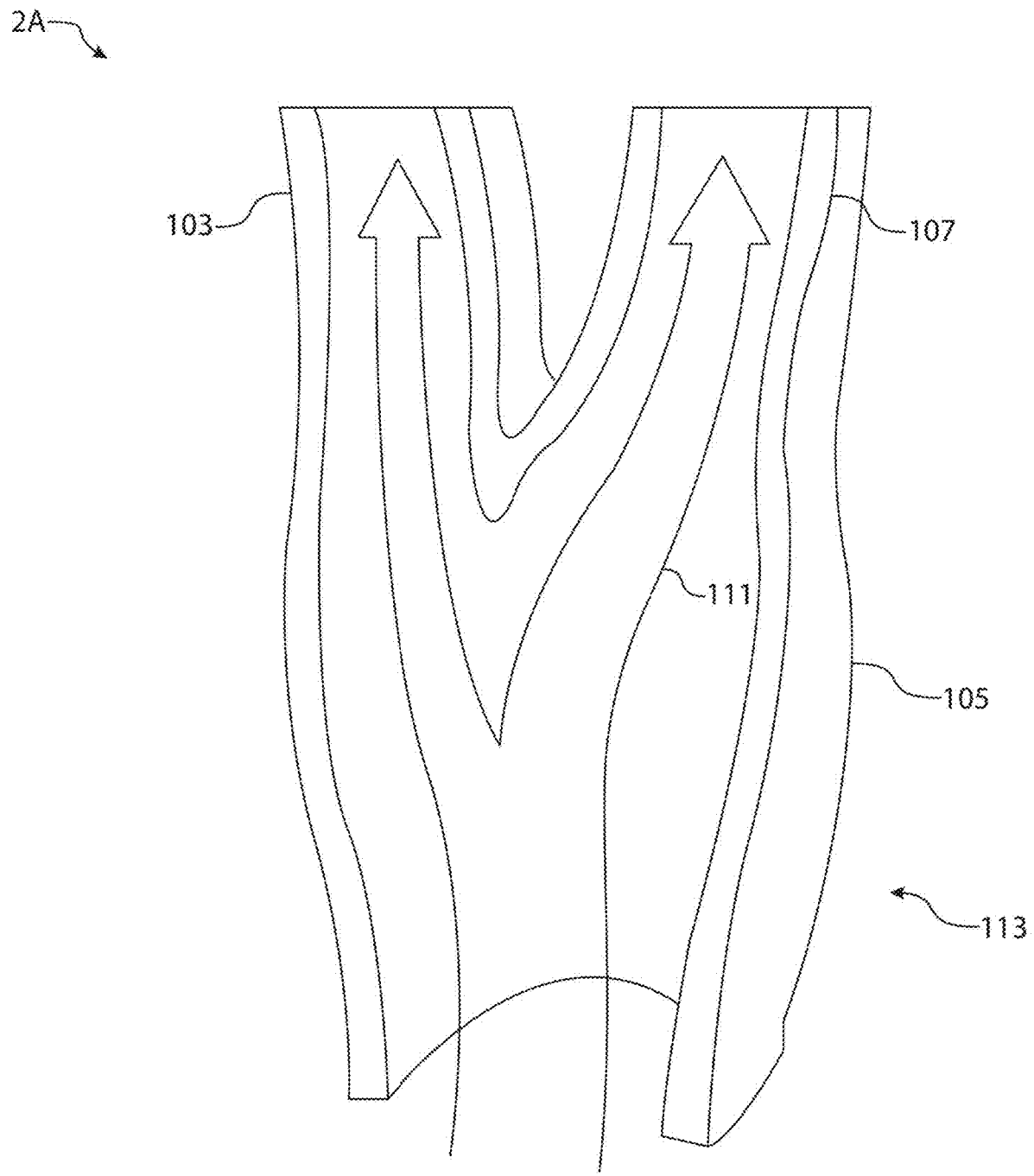
FIG. 2 is an enlarged cross-sectional view of REGION 2 in FIG. 1 depicting the blood flow in a normal, nonoccluded artery.
Figure 3:
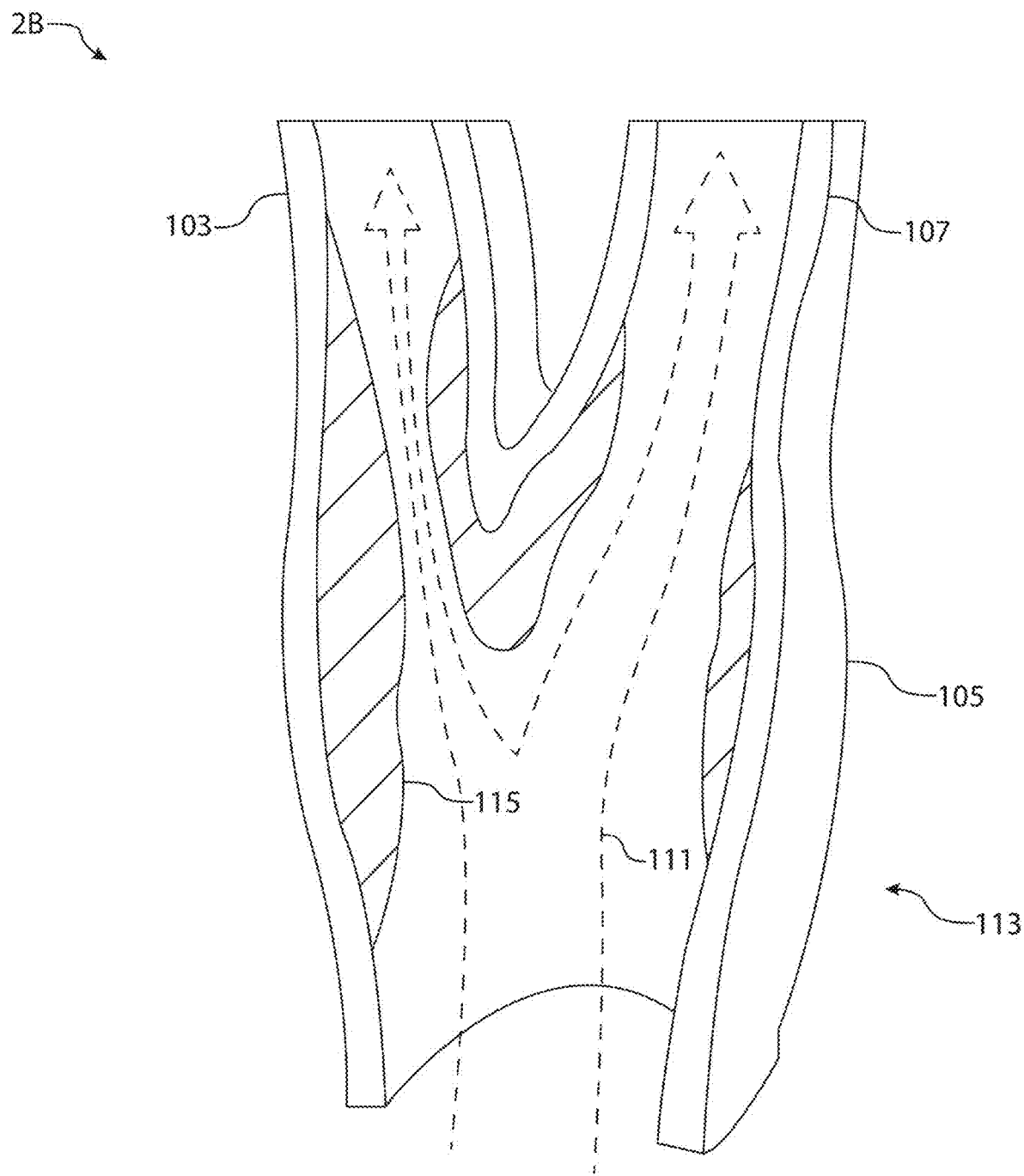
FIG. 3 is an enlarged cross-sectional view of REGION 2 in FIG. 1 depicting the blood flow in an artery occluded by plaque deposits.
Figure 4:
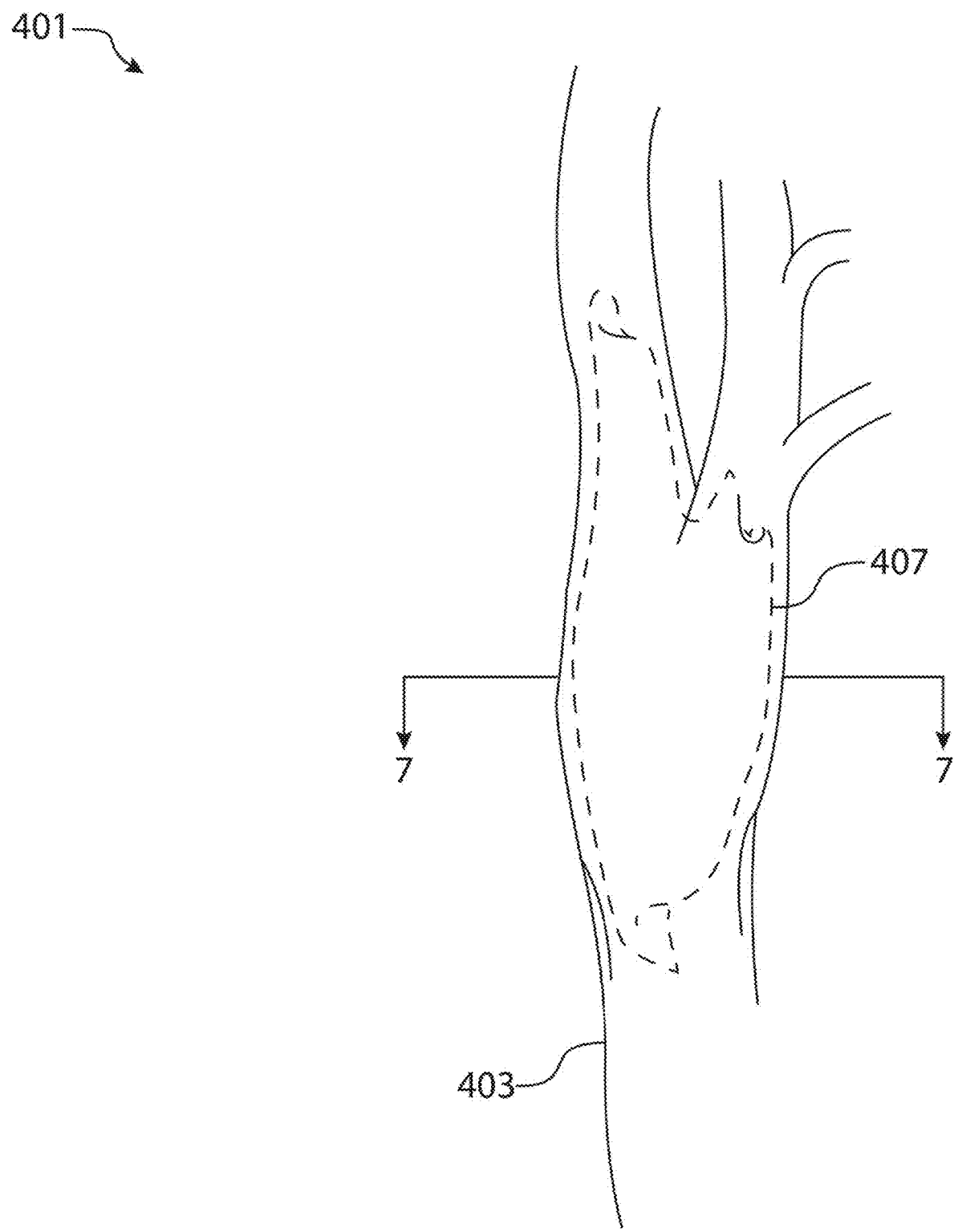
FIG. 4-8 depict a first procedure for removing plaque deposits from an occluded carotid artery.
Figure 5:
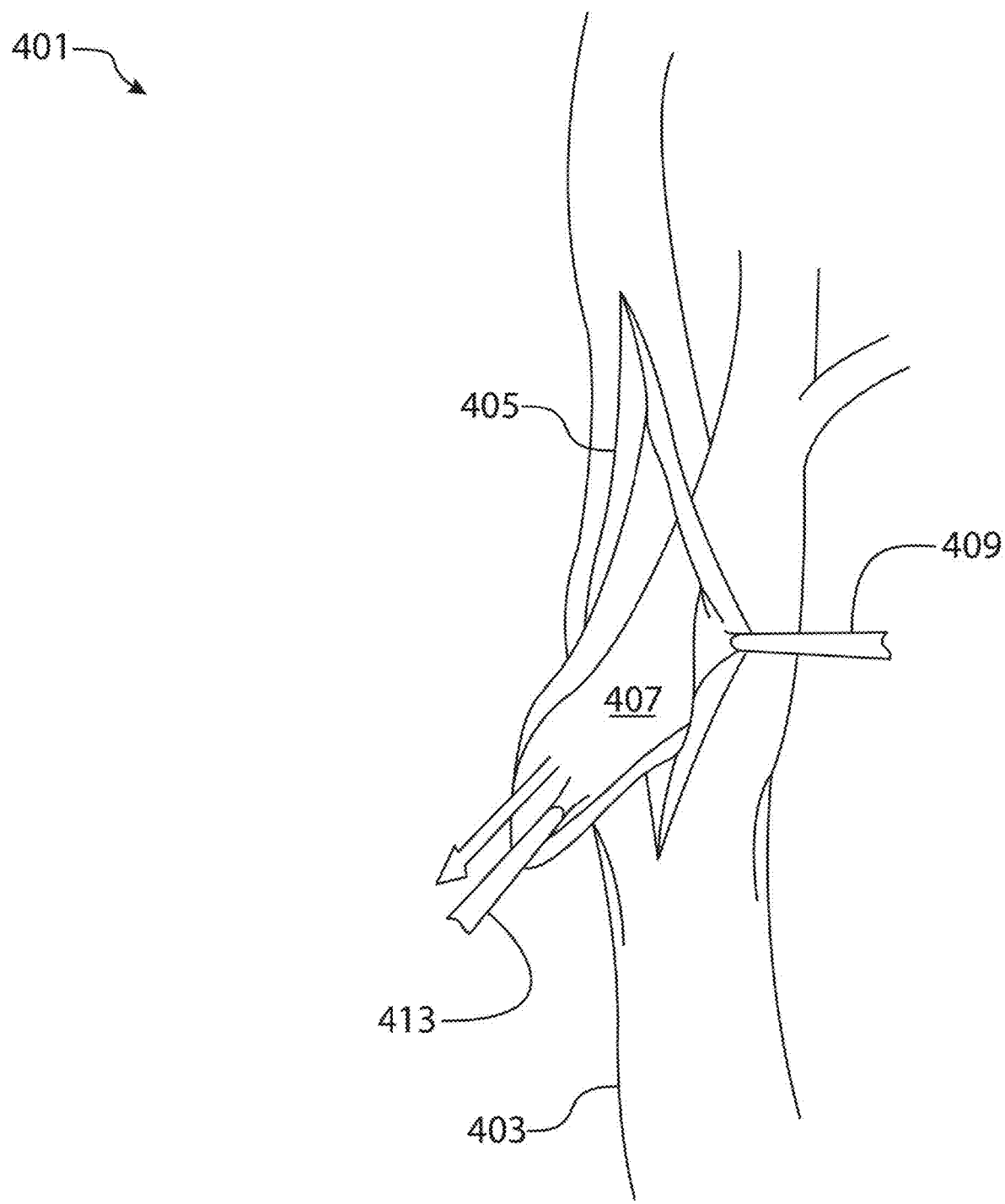
Figure 6:
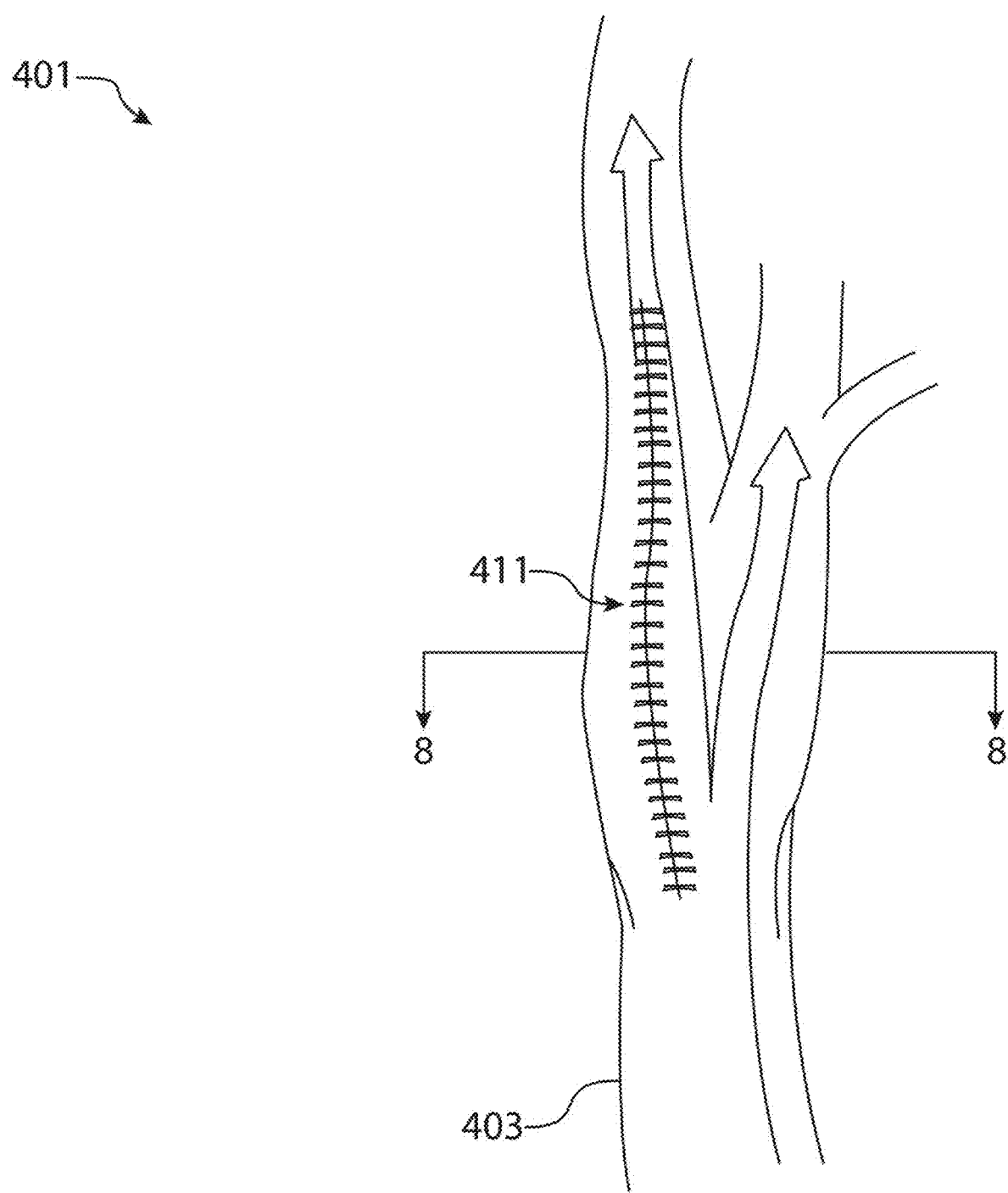
Figure 7:
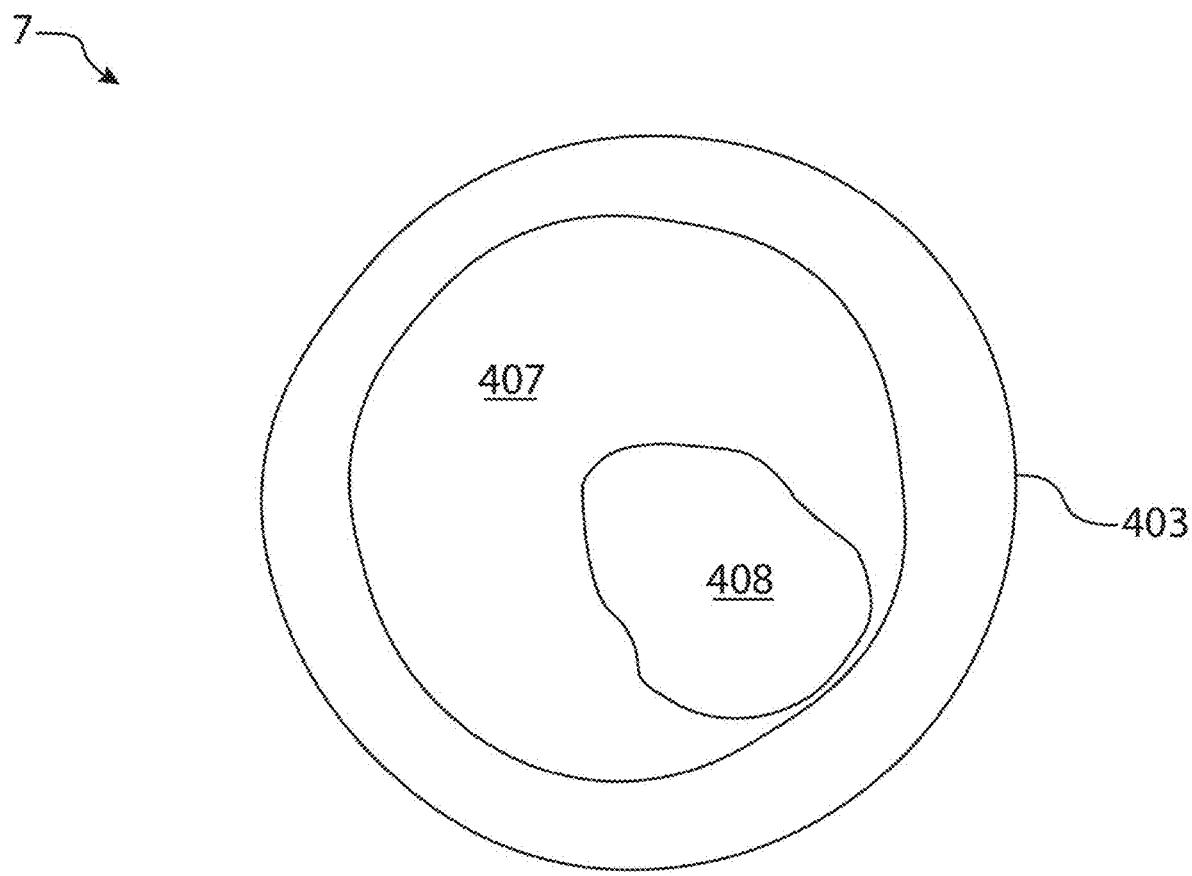
Figure 8:
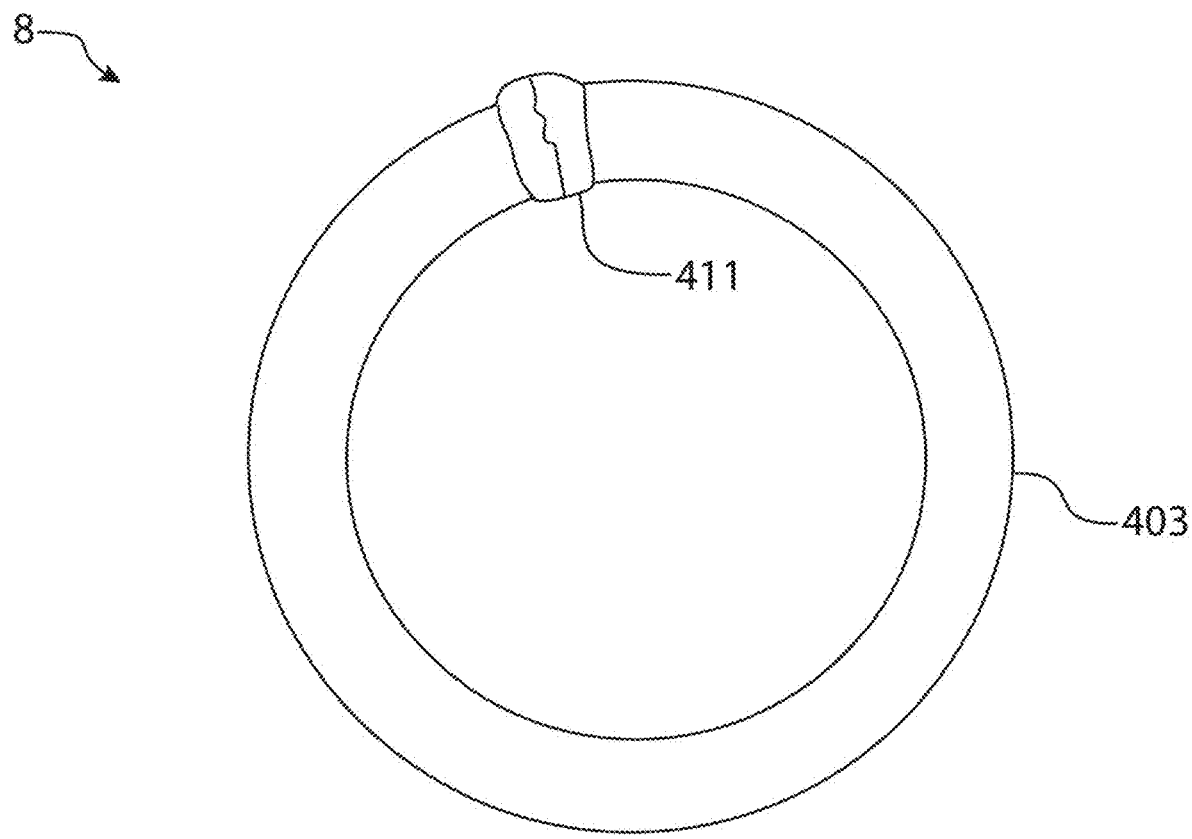
Figure 9:
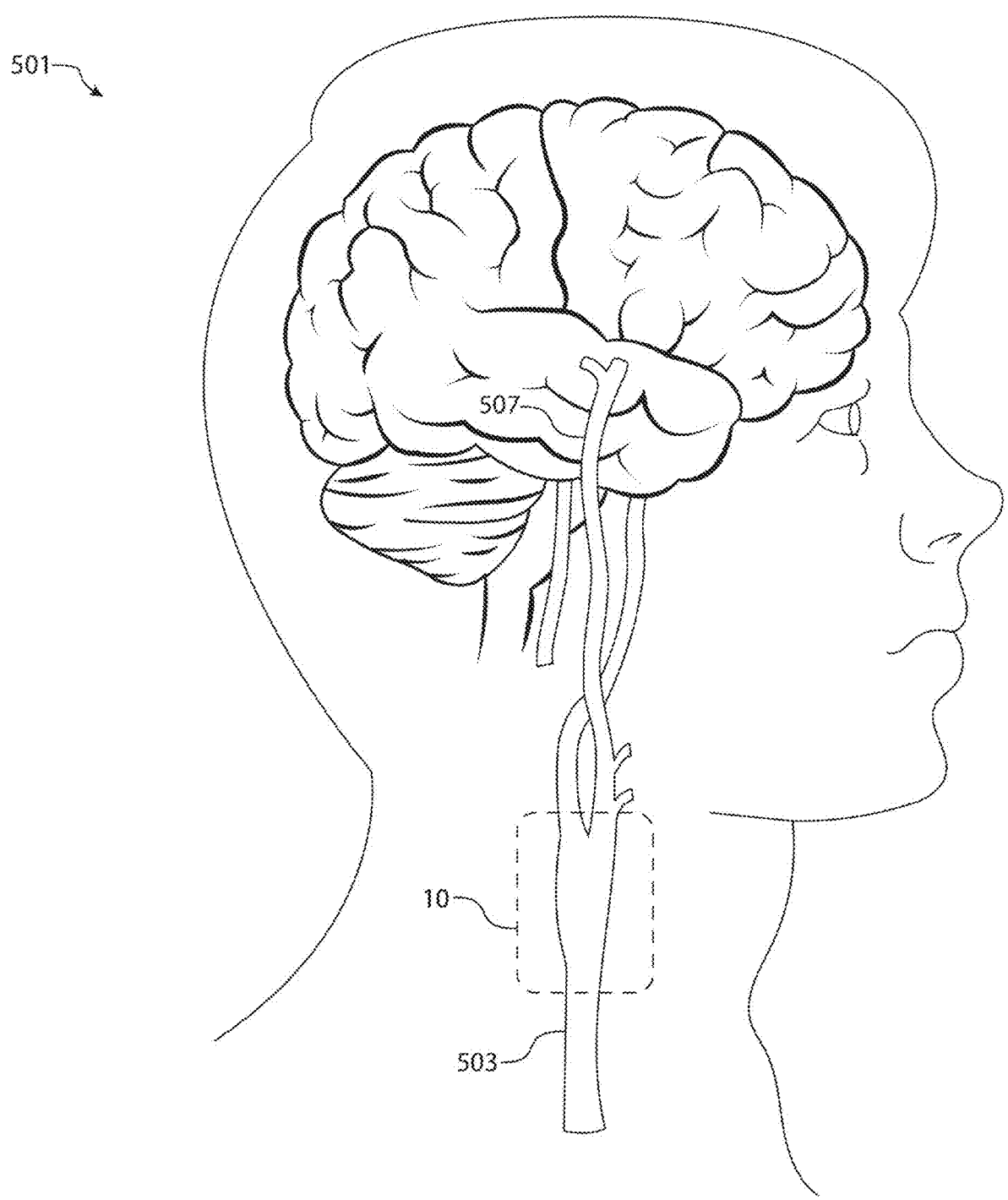
FIG. 9 is an illustration of a carotid artery in a subject, in which some elements of the physiology of the subject have been rendered transparent for purposes of illustration to show the location of the right carotid artery in the neck of a subject.
Figure 10:
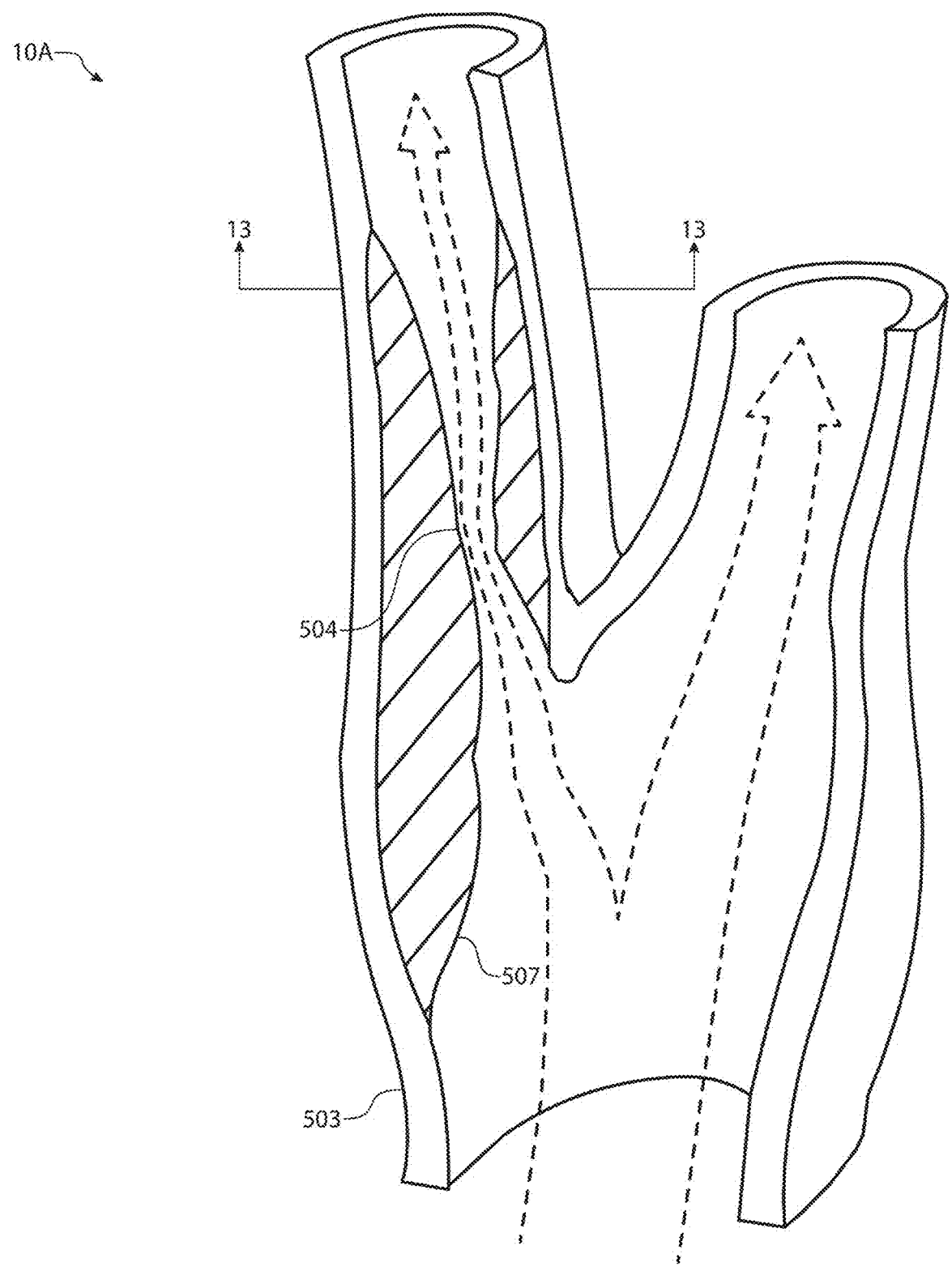
FIGS. 10-14 is a series of cross-sectional images depicting a second procedure for restoring blood flow to an occluded carotid artery (FIG. 10) through arterial stenting. The procedure involves inserting a catheter in the occluded portion of the artery (FIG. 11) and using the catheter to insert a stent which widens the occluded artery (FIG. 12), thereby restoring blood flow.
Figure 11:
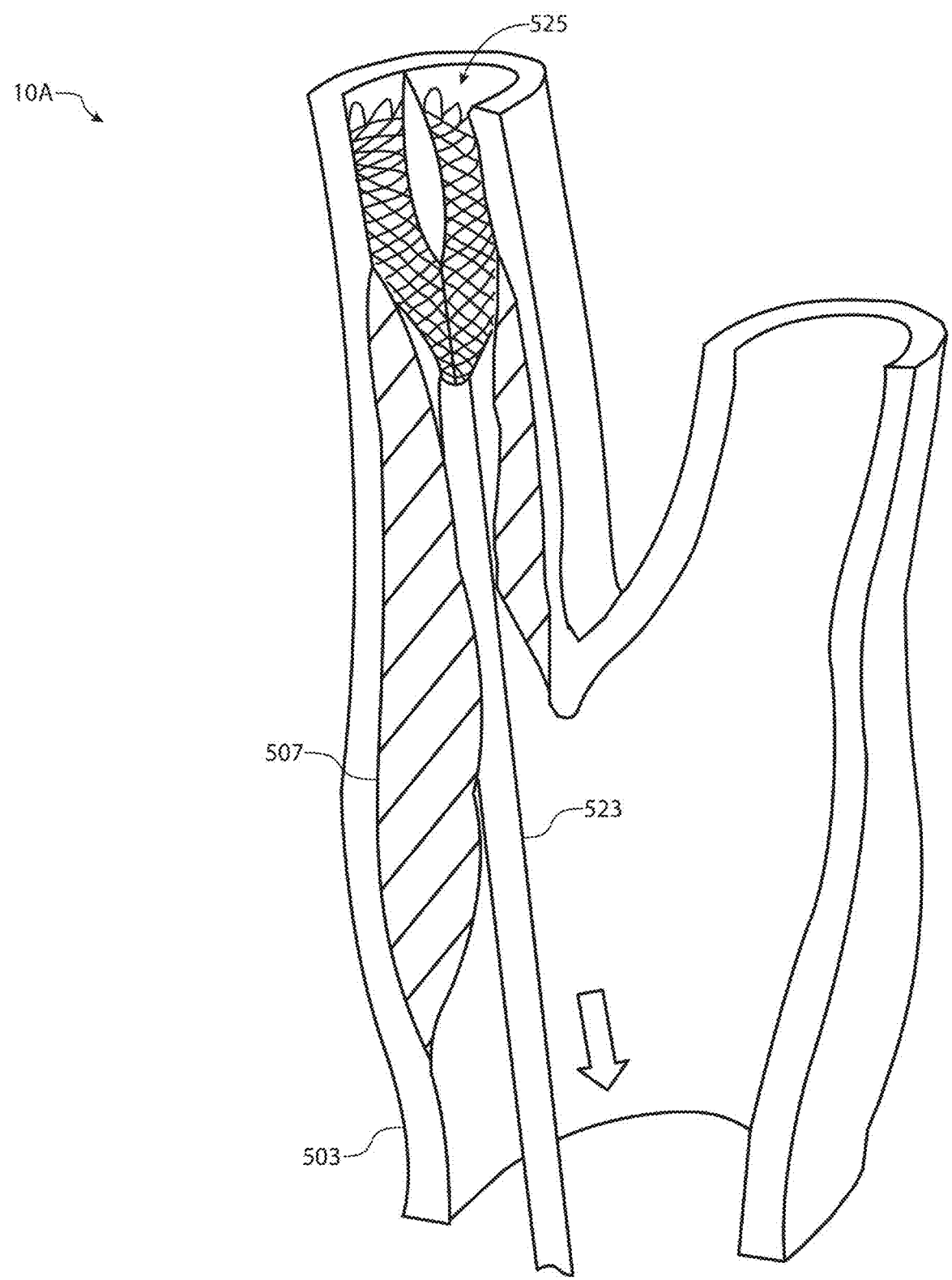

In one aspect, a method is provided for treating a subject. The method comprises performing surgery on the subject; and performing light therapy on the subject as an adjuvant to the surgery.

In another aspect, a method is provided for treating a subject. The method comprises performing a carotid endarterectomy on the subject; and performing light therapy on the subject as an adjuvant to the carotid endarterectomy.

In a further aspect, a method for treating a plaque-based arterial occlusion in a carotid artery of a subject is provided. The method comprises performing a carotid endarterectomy on the subject; and performing light therapy on the subject within 4 hours after the carotid endarterectomy.

In still another aspect, a method is provided for treating a plaque-based arterial occlusion in a carotid artery of a subject. The method comprises performing a carotid endarterectomy on the subject; determining the levels in the subject of a plurality of biomarkers $B_i \in [B_1, \ldots, B_n]$, wherein $n \geq 2$; and performing light therapy on the subject if any of the plurality of biomarkers $B_i$ has a level $x_i$ in excess of a corresponding threshold value $t_1$.

In yet another aspect, a method for treating a plaque-based arterial occlusion in a carotid artery of a subject. The method comprises performing a carotid endarterectomy on the subject; determining in a subject the levels $L_{i1}$ and $L_{i2}$ at corresponding times $t_{i1}$ and $t_{i2}$ of a plurality of biomarkers $B_i \in [B_1, \ldots, B_n]$, wherein $n \geq 2$; and performing light therapy if, for at least one biomarker $B_i$, $\Delta_i \geq k_i$, wherein $\Delta_i = L_{i2} - L_{i1}$.

In another aspect, a method for treating a plaque-based arterial occlusion in a carotid artery of a subject. The method comprises performing a carotid endarterectomy on the subject; determining in a subject the levels $L_{i1}$ and $L_{i2}$ at corresponding times $t_{i1}$ and $t_{i2}$ of a plurality of biomarkers $B_i \in [B_1, \ldots, B_n]$, wherein $n \geq 2$; and performing light therapy if $P \geq k$, wherein P is the polynomial $P = \Sigma_1^n w_i \Delta_i$, wherein $\Delta_i = L_{i2} - L_{i1}$ and wherein $w_i$ is a weighting factor.

DETAILED DESCRIPTION

Carotid endarterectomies have a well-known risk profile associated with them. In particular, about 2-3% of patients who exhibit no symptoms prior to undergoing the procedure suffer a stroke. These percentages are higher (about 5-7%) for those patients who exhibit stroke (or mini-stroke) symptoms or transient ischemic attack (TIA) prior to undergoing the procedure. The procedure also entails an increased risk of heart attack or nerve damage (especially with respect to the back, tongue or voice box of the patient).

Many patients exhibit postoperative cognitive decline (PCD) after undergoing a carotid endarterectomy. PCD may be defined as postoperative deterioration in two or more cognitive domains occurring in the postoperative period. Various estimates of the incidence of PCD attendant to carotid endarterectomies may be found in the literature, and are typically given as 6 to 30%. [Heyer E J, DeLapaz R, Halazun H J, et al. Neuropsychological dysfunction in the absence of structural evidence for cerebral ischemia after uncomplicated carotid endarterectomy. Neurosurgery 2006; 58:474-479]. Some of the variance in these estimates may be due to distinctions between immediate and long-term PCD. Thus, the incidence of measurable cognitive decline after carotid endarterectomies has been estimated at about 20% for substantial immediate cognitive decline, and 14% for more serious, longer-term cognitive decline. [Paola Aceto, Carlo Lai, Franco De Crescenzo, Maria A Crea, Valeria Di Franco, Gaia R Pellicano, Valter Perilli, Silvia Lai, Domenico Papanice, Liliana Sollazzi. Cognitive decline after carotid endarterectomy: Systematic review and meta-analysis European Journal of Anaesthesiology 2019 Dec. 12]. Since carotid endarterectomies are a relatively common surgical procedure, the foregoing demonstrates that PCD is a significant medical problem which affects a large number of patients.

The incidence of PCD may be higher in patients with certain risk factors or profiles. Thus, for example, patients undergoing carotid endarterectomies for symptomatic left internal carotid artery (LICA) stenosis have been found to have a greater risk of PCD than patients with asymptomatic LICA disease or right internal carotid artery (RICA) disease. [Bo M, Massaia M, Speme S, et al. Risk of cognitive decline in older patients after carotid endarterectomy: an observational study. J Am Geriatr Soc. 2006; 54(6):932-936]. Moreover, patients with significant pre-operative anxiety have been found to have a higher probability of suffering from PCD. [Du J, Plas M, Absalom A R, van Leeuwen B L, de Bock G H. The association of preoperative anxiety and depression with neurocognitive disorder following oncological surgery J Surg Oncol. 2020; 121(4):676-687].

Light therapy in general, and photobiomodulation therapy (PBMT) in particular, have received considerable attention over the years, although their potential application as adjuvants to surgical procedures has not heretofore been appreciated. PBMT is a type of light therapy that utilizes non-ionizing electromagnetic energy to trigger photochemical changes in cellular structures that are receptive to photons. Various devices have been developed in the art to implement PBMT or processes related thereto. Examples of such devices are described, for example, in U.S. 2019/0246463A1 (Williams et al.), U.S. US2019/0175936 (Gretz et al.), WO2019/053625 (Lim), U.S. U.S. 2014/0243933 (Ginggen), U.S. 2019/0142636 (Tedford et al.), U.S. Pat. No. 7,354,432 (Eells et al.), U.S. 2008/0091249 (Wang), U.S. Pat. No. 10,391,330 (Bourke et al.) and U.S. 2016/0129278 (Mayer).

Although the effects of PBMT are not fully understood, the underlying physiological processes at play during PBMT have been the subject of considerable research. Mitochondria are thought to be central to these processes. These intracellular organelles generate adenosine triphosphate (ATP), which is the main source of energy for cellular activity and metabolism.

Mitochondria absorb visible red and near infrared light (NIR) at the cellular level, and utilize the absorbed radiation to produce cellular energy in the form of ATP. A mitochondrial enzyme (cytochrome oxidase c) is central to this process. This enzyme is a chromophore, and accepts photonic energy of specific wavelengths when functioning below photosynthetically active radiation (PAR).

The process utilized by mitochondria to generate ATP also creates reactive oxygen species (ROS). These species promote gene transcription, cellular repair and healing. This process is also believed to release nitric oxide back into the body. Nitric oxide helps cells to communicate with each other, and also improves blood circulation and dilates blood vessels.

Some benefits of photobiomodulation therapy (PBMT) have been recognized in the art. For example, a recent study by Iaccarino et al. [Iaccarino, H. F., Singer, A. C., Martorell, A. J., Rudenko, A., Gao, F., Gillingham, T. Z., . . . Tsai, L. H. (2016), "Gamma Frequency Entrainment Attenuates Amyloid Load and Modifies Microglia", Nature, 540(7632), 230-235)] indicated that the non-invasive method of flickering light which is disclosed therein may induce gamma waves in the brain, and may reduce pathological symptoms of Alzheimer's disease (AD). In this study, mice that were genetically engineered to develop AD were exposed to an LED light source that flickered at 40 Hertz (Hz). After treatment with the oscillating light source for one hour, the mice showed reduction of amyloid beta (AP) plaque levels in the visual cortex by half (Aβ plaques are thought to be associated with AD). In another study [Koster, M et al. (2019), "Memory Entrainment by Visually Evoked Theta-Gamma Coupling", Neuroimage 188, 181-18785], visual theta stimulation was found to lead to enhanced memory performance. Despite these studies, however, many of the possible effects of PBMT remain unknown.

It has now been found that the risk profile associated with carotid endarterectomies and other major surgeries may be reduced through proper utilization of light therapy in conjunction with, or as an adjuvant to, the surgery. Such light therapy may include brain entrainment or PBMT, and may be implemented in conjunction with auditory stimulation such as, for example, the use of binaural beats. In particular, it has been found that light therapy in general, and PBMT in particular, may be useful in lessening the side effects (or severity of these side effects) of carotid endarterectomies including, without limitation, the incidence or severity of PCD, stroke (or mini-stroke) symptoms, TIA, heart attack, nerve damage or their sequelae. It has further been found that light therapy in general, and PBMT in particular, may be useful in treating pre-operative anxiety in some patients, thus lessening the likelihood that such patients will suffer PCD as a result of their surgeries.

In a preferred embodiment of the systems and methodologies disclosed herein, biomarkers of neuroinflammation may be utilized to identify patients who would benefit from light therapy or PBMT, or to gauge the efficacy of, or ongoing need for, light therapy or PBMT as a treatment modality for patients in pre-operative or post-operative settings. Such biomarkers (which may include, for example, certain proteins present in cerebral spinal fluid (CSF) or blood serum such as, for example, certain cytokines or chemokines) are described in [Danielson M. Wiklund A, Granath F, et al. Neuroinflammatory markers associate with cognitive decline after major surgery. Findings of an explorative study. Ann Neurol. 2020; 87(3):370-382], which is incorporated herein by reference in its entirety. Specific examples of biomarkers which may be utilized for this purpose may include one or more bio markers selected from the group consisting of IL6, IL8, CCL3, CCL8, and CXCL6. It will be appreciated that, to the extent light therapy or PBMT may be utilized as an anti-inflammatory treatment immediately after surgery, the use of these treatments may beneficially affect the long-term cognitive outcome of patients who undergo carotid endarterectomies or other major surgical procedures.

Various other factors may also be utilized to identify patients who may benefit from light therapy or PBMT. These include patients suffering from postoperative pain, sleep disturbances, and certain drug effects.

In a preferred embodiment of the methodologies disclosed herein, a subject is diagnosed as suffering from a condition for which a carotid endarterectomy is indicated. A light therapy unit is then provided which preferably comprises (a) a chassis, (b) a plurality of lights or LEDs disposed on the chassis, and (c) a controller which controls the operation of said lights or LEDs. The light therapy unit is then positioned in a therapeutically effective orientation with respect to the subject (or alternatively, the subject is positioned in a therapeutically effective orientation with respect to the light therapy unit). The plurality of lights or LEDs are then operated at one or more of first, second and third distinct wavelengths of light (and preferably at red, near-infrared and blue-turquoise wavelengths) such that the light emitted by the lights or LEDs impinges on the subject. In some embodiments, one or more of the wavelengths of light may be modulated in their intensity at a frequency within the range of about 20 Hz to about 60 Hz, more preferably within the range of about 30 Hz to about 50 Hz, and most preferably at about 40 Hz. In some embodiments, the light therapy may be accompanied by one or more music or audio files, which may include a track or portion thereof which may be modulated at a frequency within the range of about 20 Hz to about 60 Hz, more preferably within the range of about 30 Hz to about 50 Hz, and most preferably at about 40 Hz.

Figure 15:
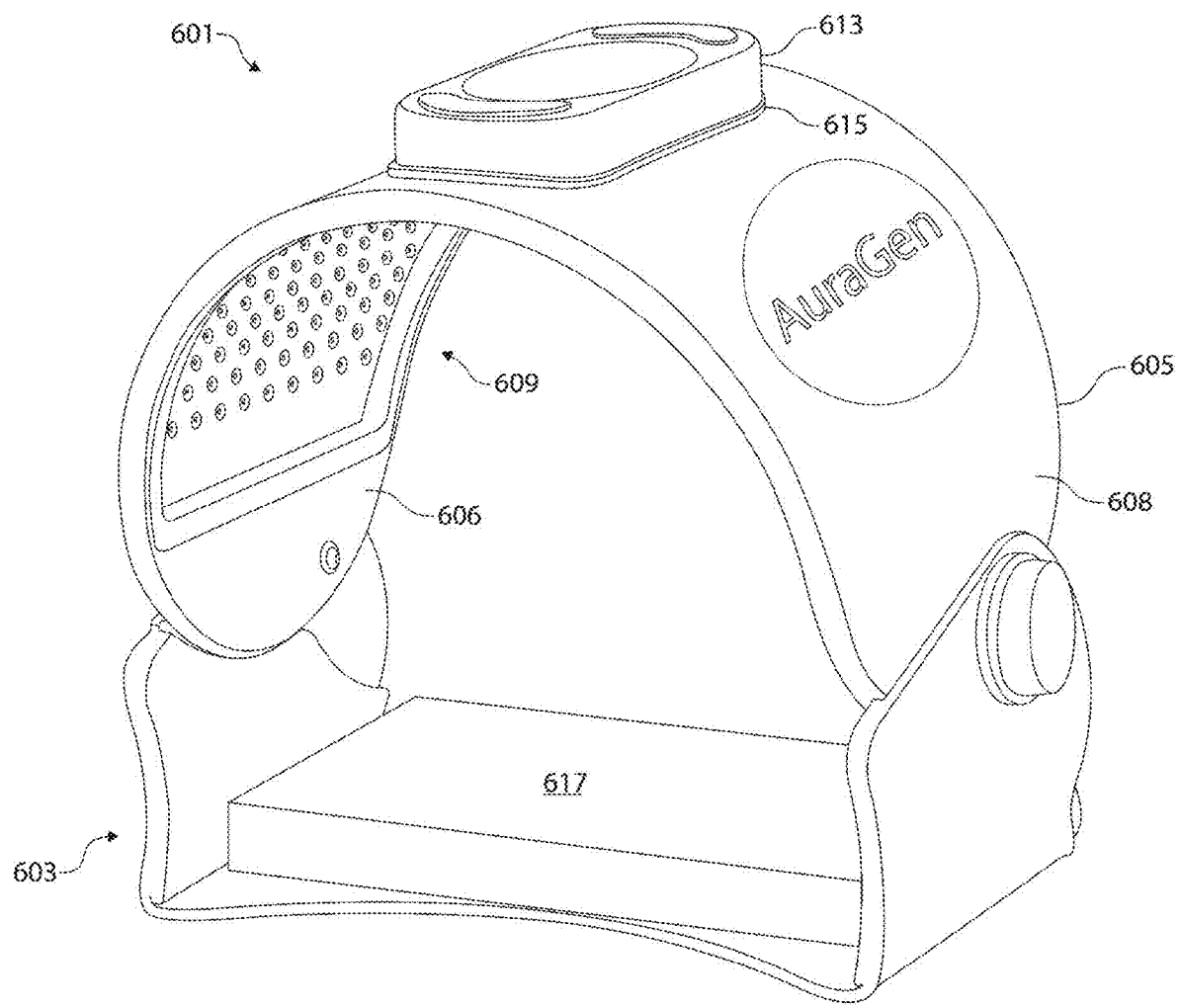
FIGS. 15-17 depict a light therapy unit which may be utilized to implement the devices and methodologies disclosed herein.
Figure 16:
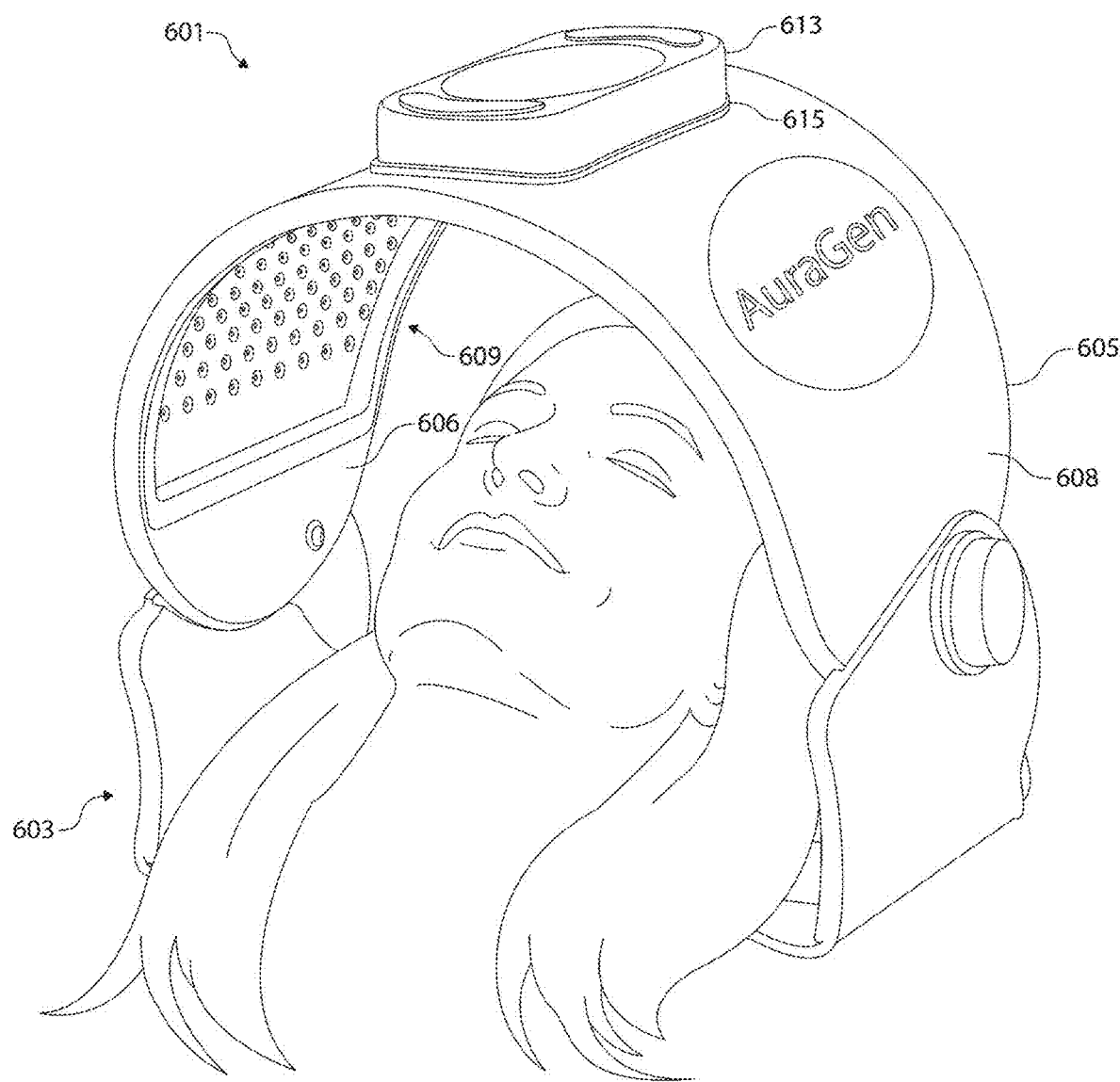
Figure 17:
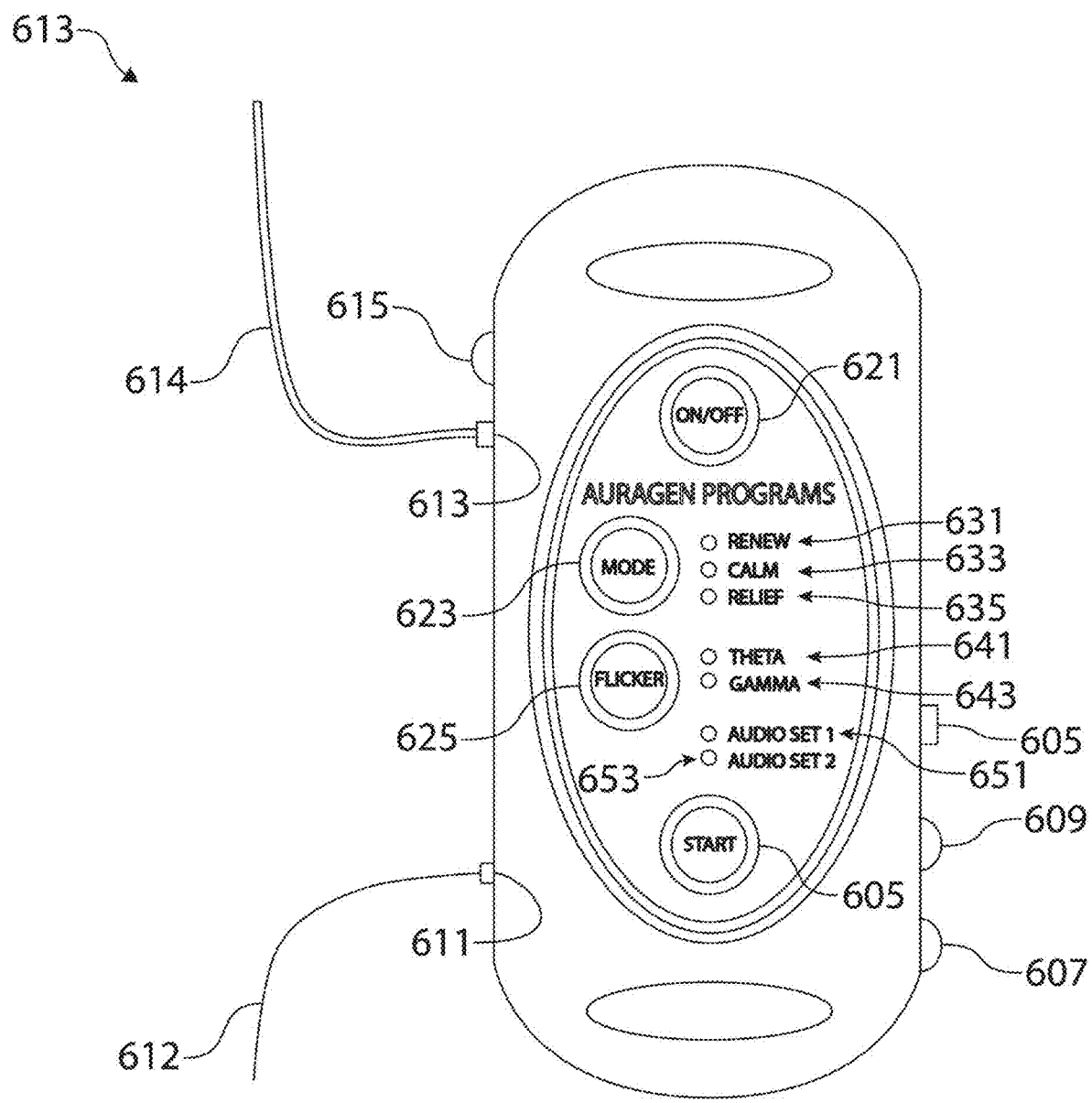

Various devices may be utilized to implement light therapy or open-loop brainwave entrainment in accordance with the teachings herein, and using any of various waveforms. FIGS. 15-17 illustrate a particular, nonlimiting embodiment of such a device. The device 601 depicted therein comprises a base 603 having a peripheral element 605 attached thereto and, optionally, an audio headset (not shown; the need for a headset may be determined, for example, by whether an entrainment methodology is employed that uses traveling waves originating from the same source, or standing waves generated by two distinct sources). The base 603 and peripheral element 605 define an opening 607 in which a user's head is placed (see FIG. 17). The base 603 and/or peripheral element 605 may be equipped with an audio jack, a Bluetooth transmitter, or other suitable provisions as necessary or desirable to support the use of an audio headset by the user.

The base 603 in this particular embodiment is equipped with a pillow 617 for user comfort, and to provide the user with the ability to lie down or sleep during a light therapy or brainwave entrainment session. The peripheral element 605 has a first major inward-facing surface 606 and a second major outward-facing surface 608. The first major surface 606 is equipped with an LED array 609 which can be activated with a remote control 613 to illuminate the user's head or body at one or more wavelengths. The second major surface 608 is equipped with a holder 615 for the remote control 613. The remote control 613, which is shown in greater detail in FIG. 17, may also be utilized to modulate the light emitted by the LED array 609, to select one or more wavelengths of light emitted by the LED array 609, and to control the playback of one or more audio files or tracks.

Figure 12:
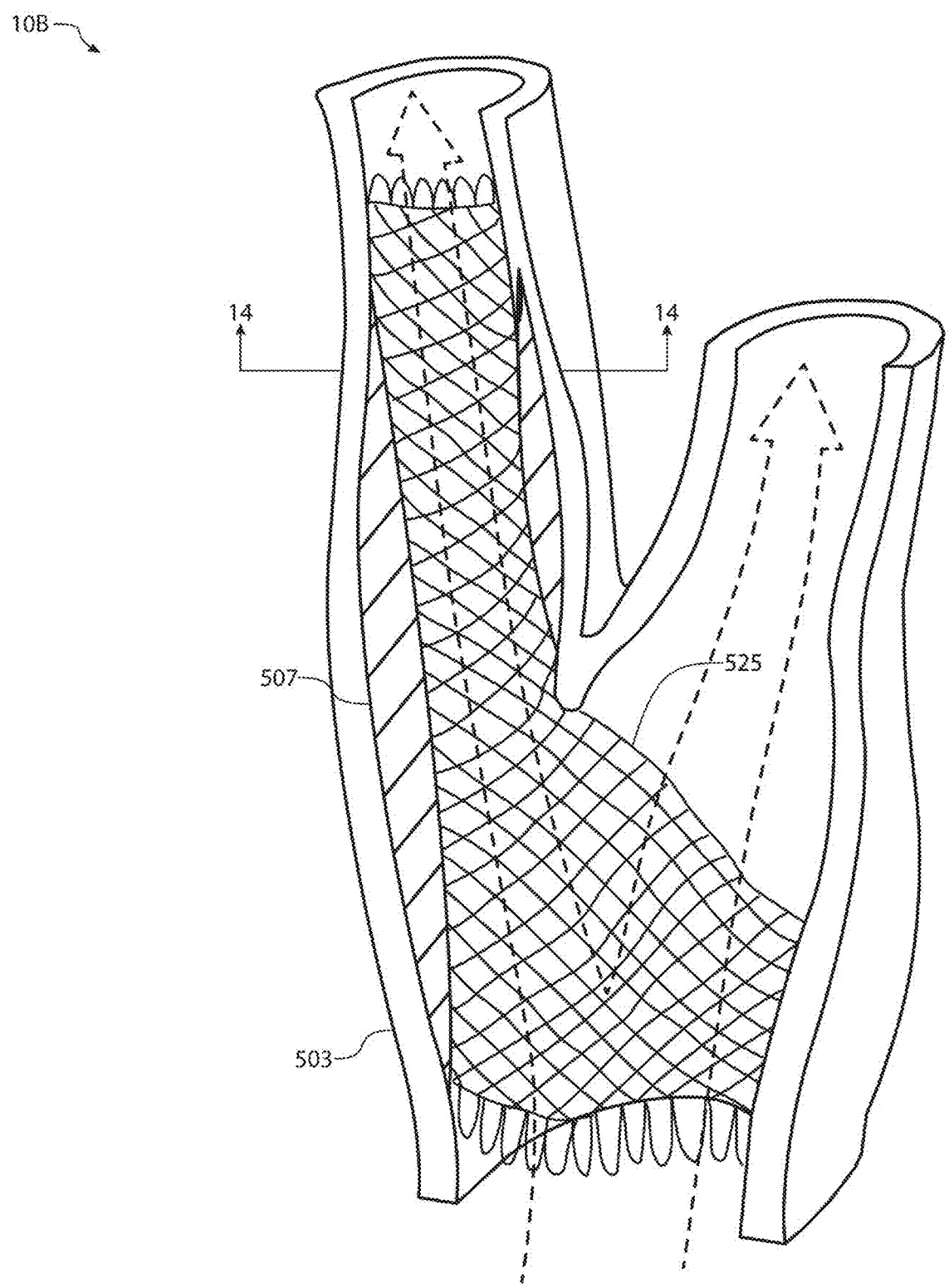
Figure 13:
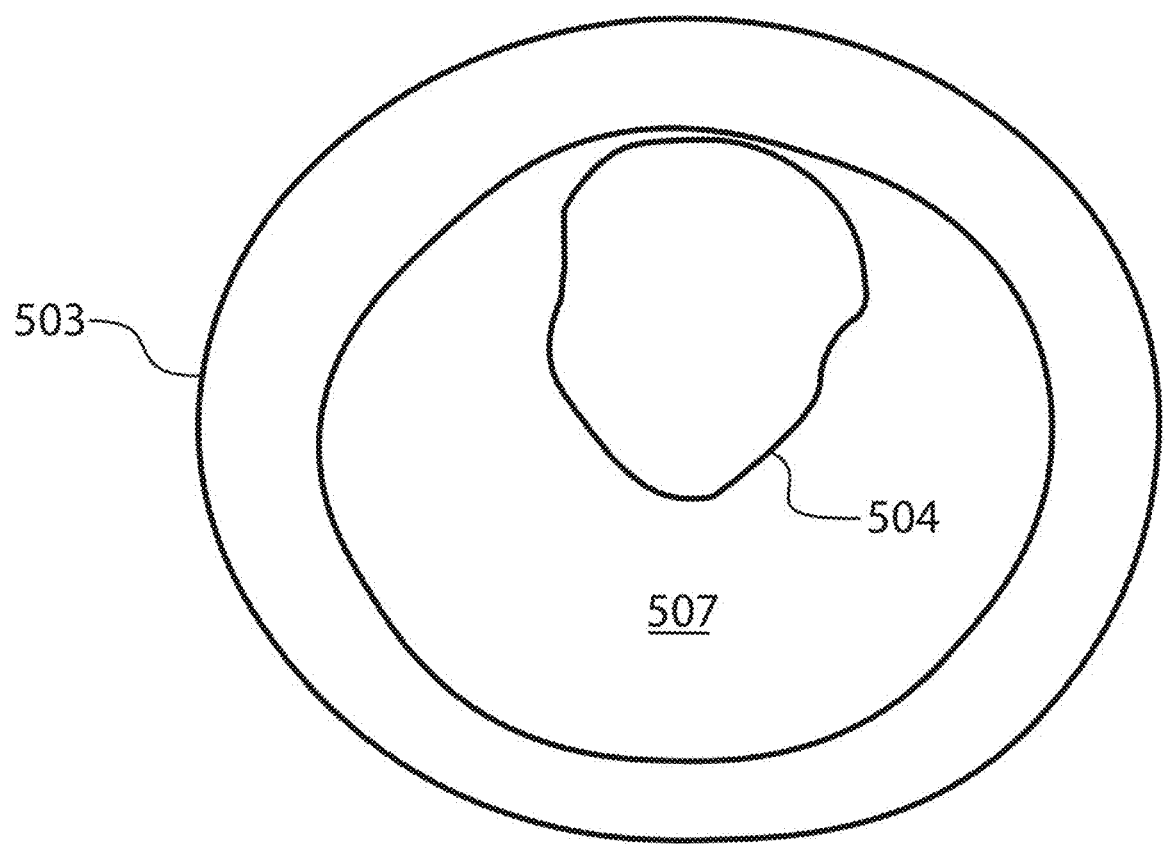
Figure 14:
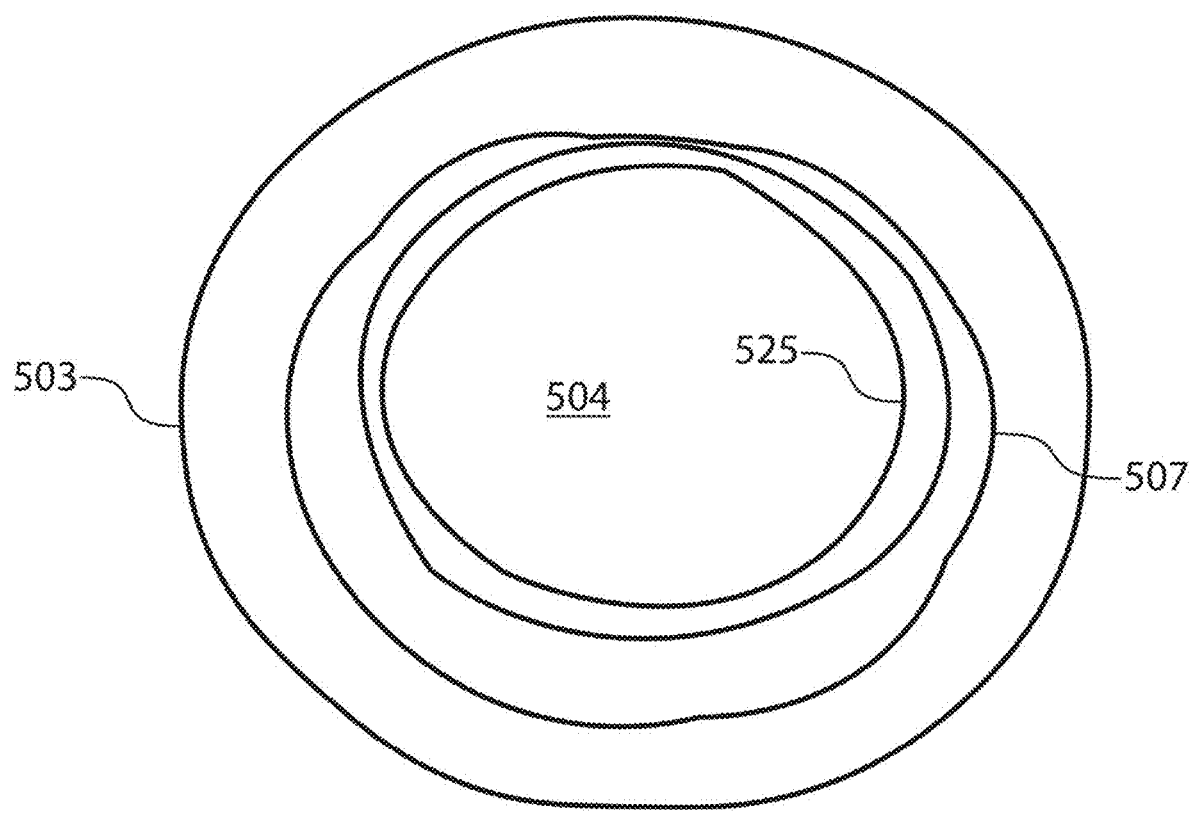

FIG. 17 depicts a particular, non-limiting embodiment of a remote control 613 that may be utilized with the light therapy device 601 of FIGS. 12-14. The remote control 613 comprises a body 671 which houses the electronics of the remote control 613, which will typically include an appropriate chipset and other suitable control circuitry. The remote control 613 is equipped with a central keypad 673 and peripheral controls, the latter of which include a track selection 605 for selecting one of a plurality of prerecorded audio tracks, a first volume control 607 for adjusting the audio volume of the selected audio track, and a second volume control 609 for controlling the volume of a second soundtrack featuring a sound at a specific frequency (for example, a gamma or beta frequency), which may be a diurnal beat. The two soundtracks may be played together or independently of each other.

The remote control 613 is further equipped with a headset audio plug-in port 611 for connecting a wired headset 612 to the remote control 613, and a power plug-in port 613 for connecting a power cord 614 to the remote control 613. The power cord 614 may be utilized to power the remote control 613 or to recharge one or more internal batteries contained within the device. The remote control 613 is also equipped with an LED indicator 615 to indicate when it is in a powered-on state.

The central keypad 673 includes an on/off button 621 which turns the remote control 613 on and off. A mode button 623 allows the user to toggle among mode selections (here, "Renew" 631, "Calm" 633 and "Relief" 635 mode selections), wherein each mode operates the light therapy device 601 (see FIG. 15) in accordance with a particular program. A flicker button 625 allows the user to toggle among flicker settings. In the particular embodiment depicted, the flicker button 625 allows the user to select flickering at theta 641 or gamma 643 frequencies, or to deactivate flickering altogether. In the particular embodiment depicted, the central keypad 673 also includes audio set indicators which track which of a plurality of audio sets (here, audio set 1 651 and audio set 2 653) the track selection button 605 is sampling audio tracks from.

In use, a user's head is placed in the opening 607 such that the back of the user's head is on the pillow 611 and such that the user is facing the first major surface 606 of the peripheral portion 605 as shown in FIG. 16. The user (or possibly a clinician or other assistant) then uses the remote control 613 to activate the device 601 and to cause it to function in one or more selected modes. Regarding the latter, it is to be noted that the device 601 may be programmed with various algorithms which cause it to function in particular ways, some of which are described in greater detail below. The device 601 may also be programmed to play music or soundtracks, which may be advantageously matched to the particular algorithm being implemented by the device 601.

In some embodiments, the entrainment device may include a port to allow plugin of additional, preferably portable devices which may contain one or more lights or LEDs and which may be place in the mouth of the user (via, for example, a mouth guard). In other embodiments, the device may include a small pad that may be wrapped or directly applied to a specific body part of the user, or a device that may be inserted into one or both nostrils of the user. In still other embodiments, the device may include a set of googles or glasses that are placed over the eyes of the user to provide focused treatment to those areas, or to prevent treatment of those areas. Of course, it will be appreciated that any of the foregoing accessories may be utilized in combination in various embodiments of the systems and methodologies disclosed herein.

Various LEDs 609 or other light sources which emit at various wavelengths may be utilized in the devices and methodologies disclosed herein. However, the use of light sources which emit at wavelengths in the red, infra-red and blue-turquoise regions of the spectrum are preferred, and the use of light sources which emit at about 470 nm, 670 nm and 870 nm are especially preferred. In a preferred mode of operation, these light sources are made to oscillate or flicker in the theta or gamma band. Devices of this type are described, for example, in U.S. Ser. No. 17/195,068 (Barron et al.), filed on Mar. 8, 2021, and entitled "SYSTEMS AND METHODOLOGIES FOR TREATING OR PREVENTING PSYCHIATRIC DISORDERS, BRAIN TRAUMA, AND ADDICTION OR DEPENDENCE BY LIGHT THERAPY WITH MODULATED FREQUENCY"; PCT/US21/42675 (Fortkort et al.), filed on Jul. 22, 2021, and entitled "SYSTEMS AND METHODOLOGIES FOR PERFORMING BRAINWAVE ENTRAINMENT USING NESTED WAVEFORMS"; PCT/US21/45829 (Fortkort et al.), filed on Aug. 12, 2021, and entitled "THERAPEUTIC DEVICE UTILIZING ELECTROMAGNETIC RADIATION WITH OSCILLATING POLARIZATION STATE"; and U.S. 63/235,692 (Fortkort et al.), filed on Oct. 27, 2021, entitled "LIGHT THERAPY TREATMENT MODALITY WITH OSCILLATING AND NONOSCILLATING WAVELENGTHS"; all of which are incorporated herein by reference in its entirety.

It will be appreciated that light may be emitted at the foregoing wavelengths in various manners, including sequentially or simultaneously. For example, the LED array 609 may be operated to emit electromagnetic radiation at a single wavelength (i.e., monochromatically) or at multiple wavelengths. In some cases, the LED array 609 may include a first set of LEDs that are operated to emit light at a first wavelength, a second set of LEDs that are operated to emit light at a second wavelength, and (optionally) a third set of LEDs that are operated to emit light at a third wavelength. In other cases, the LED array 609 may be operated such that all of the LEDs in the array emit light at a first wavelength for a first period of time, all of the LEDs in the array emit light at a second wavelength for a second period of time, and (optionally) all of the LEDs in the array emit light at a third wavelength for a third period of time. Still other embodiments are possible in which first, second and/or third groups of LEDs in the LED array are made to emit light at first, second and third respective wavelengths for first, second and third respective periods of time.

The particular wavelength(s) of emission of the LED array 609, the duration of those emissions, the frequency of oscillation (if any), the intensity of the emitted light, the selection of accompanying audio tracks or files (if any), and/or the oscillation of any accompanying audio tracks, files or component(s) thereof, may be selected to achieve a desired physiological or psychological effect. It will be appreciated that, in some embodiments, the duration of emission for any particular wavelength of light may remain constant or may vary during the course of a therapy session. It will further be appreciated that, in some embodiments, any of the LEDs in the LED array 609 may be operated to emit two or more wavelengths of light, including broadband radiation or white light.

Example 1

This example, which is reproduced from [Danielson M, Wiklund A, Granath F, et al. Neuroinflammatory markers associate with cognitive decline after major surgery: Findings of an explorative study. Ann Neurol 2020,87(3)-370-382], illustrates postoperative changes in cerebrospinal fluid (CSF) levels of 2 cytokines (IL6 and IL8) and 3 chemokines (CCL3, CCL8, and CXCL6) with respect to neurocognitive outcome.

Figure 19:
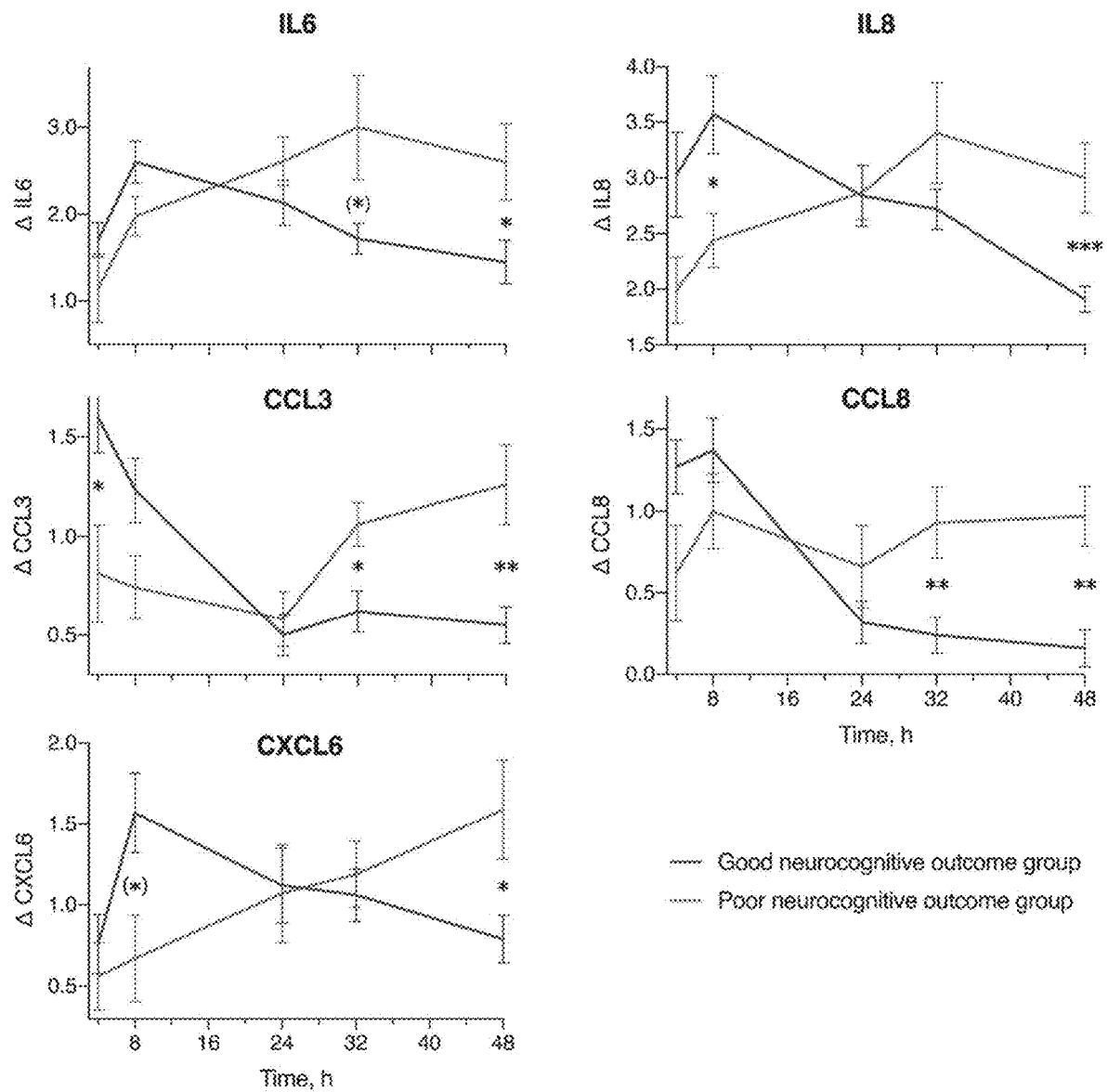
FIG. 19 is a series of graphs reproduced from [Danielson M, Wiklund A, Granath F, et al. Neuroinflammatory markers associate with cognitive decline after major surgery: Findings of an explorative study. Ann Neurol. 2020; 87(3):370-382], which depict postoperative changes in cerebrospinal fluid (CSF) levels of 2 cytokines (IL6 and IL8) and 3 chemokines (CCL3, CCL8, and CXCL6) with respect to neurocognitive outcome.

Postoperative changes in cerebrospinal fluid (CSF) levels of 2 cytokines (IL6 and IL8) and 3 chemokines (CCL3, CCL8, and CXCL6) with respect to neurocognitive outcome were assessed in a group of 24 post-surgical patients. The results are depicted in FIG. 19.

In patients with good neurocognitive outcome at 3 months, increased CSF levels of the biomarkers were seen 4 to 8 hours after surgery followed by a resolution at 32 and 48 hours. In contrast, in patients with long-term cognitive decline, CSF biomarker levels increased over time and were higher at the later phase (32 and 48 hours) post-surgery compared to patients without long-term cognitive decline (good).

In some embodiments of the methodologies disclosed herein, the level of at least one biomarker may be determined. The biomarker is preferably selected from the group consisting of cytokines and chemokines. Light therapy may be performed on the subject if the at least one biomarker is outside of a predetermined range or is above a predetermined threshold value. For example, in some embodiments, the levels $L_{i1}$ and $L_{i2}$ at corresponding times $t_{i1}$ and $t_{i2}$ of at least one biomarker $B_i$ may be determined, and the step of performing the light therapy may be repeated if $\Delta_i \geq k_i$ for threshold value $k_i$, wherein $\Delta_i = L_{i2} - L_{i1}$. In other embodiments, the levels in the subject of a plurality of biomarkers $B_i \in [B_1, \ldots, B_n]$ may be determined, wherein $n \geq 2$, and the step of performing the light therapy may be repeated if any of the plurality of biomarkers $B_i$ has a level $x_i$ in excess of a corresponding threshold value $T_i$. In still other embodiments, the levels $L_{i1}$ and $L_{i2}$ of a plurality of biomarkers $B_i \in [B_1, \ldots, B_n]$, wherein $n \geq 2$, may be determined in a subject at corresponding times $t_{i1}$ and $t_{i2}$, and the step of performing the light therapy may be repeated if, for at least one biomarker $B_i$, $\Delta_i \geq k_i$, wherein $\Delta_i = |L_{i2} - L_{i1}|$. In yet other embodiments, the levels $L_{i1}$ and $L_{i2}$ of a plurality of biomarkers $B_i \in [B_1, \ldots, B_n]$, wherein $n \geq 2$, may be determined in a subject at corresponding times $t_{i1}$ and $t_{i2}$, and the step of performing the light therapy may be repeated if $P \geq k$, wherein $P$ is the polynomial $P = \sum_1^n w_i \Delta_i$, wherein $\Delta_i = L_{i2} - L_{i1}$ (and preferably, wherein $\Delta_i = |L_{i2} - L_{i1}|$) and wherein $w_i$ is a weighting factor.

In any of the foregoing methods, the at least one biomarker is preferably selected from the group consisting of cytokines and chemokines. More preferably, the at least one biomarker may be selected from the group consisting of IL6, IL8, CCL3, CCL8 and CXCL6; the at least one biomarker may be a cytokine selected from the group consisting of IL6 and IL8; or the at least one biomarker may be a chemokine selected from the group consisting of CCL3, CCL8 and CXCL6.

In some embodiments, the at least one biomarker includes IL6, wherein the corresponding threshold value is $k_{IL6}=0$, and wherein $\Delta_{IL6}$ is measured at corresponding times (in hours post-surgery) $t_1=24$ and $t_2=32$. In other embodiments, the at least one biomarker includes IL6, wherein $k_{IL8}=0$, and wherein $\Delta_{IL8}$ is measured at corresponding times (in hours post-surgery) $t_1=24$ and $t_2=32$. In still other embodiments, the at least one biomarker includes IL6, wherein $k_{CCL3}=0.1$, and wherein $\Delta_{CCL3}$ is measured at corresponding times (in hours post-surgery) $t_1=24$ and $t_2=32$. In other embodiments, the at least one biomarker includes IL6, wherein $k_{CCL8}=0$, and wherein $\Delta_{CCL8}$ is measured at corresponding times (in hours post-surgery) $t_1=24$ and $t_2=32$. In further embodiments, the at least one biomarker includes IL6, wherein $k_{CXCL6}=0$, and wherein $\Delta_{CXCL6}$ is measured at corresponding times (in hours post-surgery) $t_1=24$ and $t_2=32$.

In some embodiments, the light therapy disclosed herein may include PBMT. In some embodiments, the light therapy may be utilized in conjunction with auditory stimulation, which may include binaural beats.

Various aspects of the systems and methodologies described herein have been described above with respect to the particular, non-limiting embodiments disclosed herein. It will be appreciated that these various aspects may be employed in various combinations (including various subcombinations) or permutations in accordance with the teachings herein.

For example, while the use of light sources which emit at wavelengths in the red, infra-red and blue-turquoise regions of the spectrum are preferred, and the use of light sources which emit at about 470 nm, 670 nm and 870 nm are especially preferred, it will be appreciated that the devices and methodologies disclosed herein may utilize various other frequencies or wavelengths of electromagnetic radiation to achieve desired physiological or psychological effects. These wavelengths or frequencies may be selected, for example, from the visible, infrared or ultraviolet regions of the electromagnetic spectrum.

Similarly, in a preferred mode of operation, the intensities of one or more of these light sources are made to oscillate or flicker in the theta or gamma frequency band during at least a portion of a therapy session. However, embodiments are possible in which the light sources are made to oscillate or flicker at other frequencies, or in which the light sources (or elements thereof) operate in a manner which is not time varying. Embodiments are also possible in which the light sources are made to oscillate or flicker at harmonics of the foregoing frequencies.

While the embodiment of FIGS. 15-17 is a preferred embodiment of a light therapy or brainwave entrainment device which may be utilized in the methodologies described herein, it will be appreciated that light therapy and brainwave entrainment devices of various shapes, configurations, layouts and functionalities may be utilized in the practice of the methodologies disclosed herein, and these devices may be provided with various accessories.

In some embodiments of the devices disclosed herein, measures may be taken to ensure that the light therapy or brainwave entrainment device is applied to only specific parts of the user's body, such as a user's neck or head. For example, in some embodiments, the user may be equipped with glasses or goggles such that the user's eyes or optical nerves are not exposed to the therapeutic radiation, or such that this light is concentrated on the user's eyes or optical nerves. In still other embodiments, an optical pad or other suitable means may be utilized to apply therapeutic radiation only to the back of a user's neck, or to a user's chest (alone or in combination with the application of light therapy or brainwave entrainment to the user's head).

Preferred embodiments of the devices disclosed herein are adapted to allow the user to lie down or otherwise assume a state of repose during a light therapy or brainwave entrainment session. Such embodiments may include, for example, a pillow or one or more deformable pads which support the user's head during a session. Here, it is notable that many other devices in the art which are designed for light therapy or brainwave entrainment require the user to remain in a sitting or standing position for the duration of the therapy.

In some embodiments of the devices disclosed herein, the device may be equipped with a suitable controller, which may be wireless or wired. The controller may be programmable or pre-programmed, and may be equipped with suitable programming instructions (which may include an operating system) recorded in a tangible, non-transient medium that cause the light therapy or brainwave entrainment device to operate in various modes or to perform various functions. These modes or functions may be selected or optimized for the treatment of various portions of a subject's body, or for the treatment of particular physiological or psychological conditions.

Various parameters (and ranges of these parameters) may be utilized in the light therapy and brainwave entrainment devices and methodologies disclosed herein. These include, without limitation, wavelength, frequency, entrainment waveform, energy, fluence, power, irradiance, intensity, pulse mode, treatment duration, and repetition. These parameters and their values may be selected base, for example, on the patient's condition and the specifics of the carotid endarterectomy or other surgical, medical or therapeutic procedure performed on the user.

It will be appreciated that the light therapy and brainwave entrainment devices disclosed herein, and the components thereof, may be equipped with suitable optical elements to achieve various purposes. Such optical elements (or portions thereof) may be diffusely or specularly reflective or transmissive. Suitable optical elements may include, but are not limited to, reflective elements, polarizers, color shifting elements, filters, light guides (including, without limitation, optical fibers, light pipes and waveguides), prismatic elements, lenses (including Fresnel lenses), and lens arrays.

Figure 18:
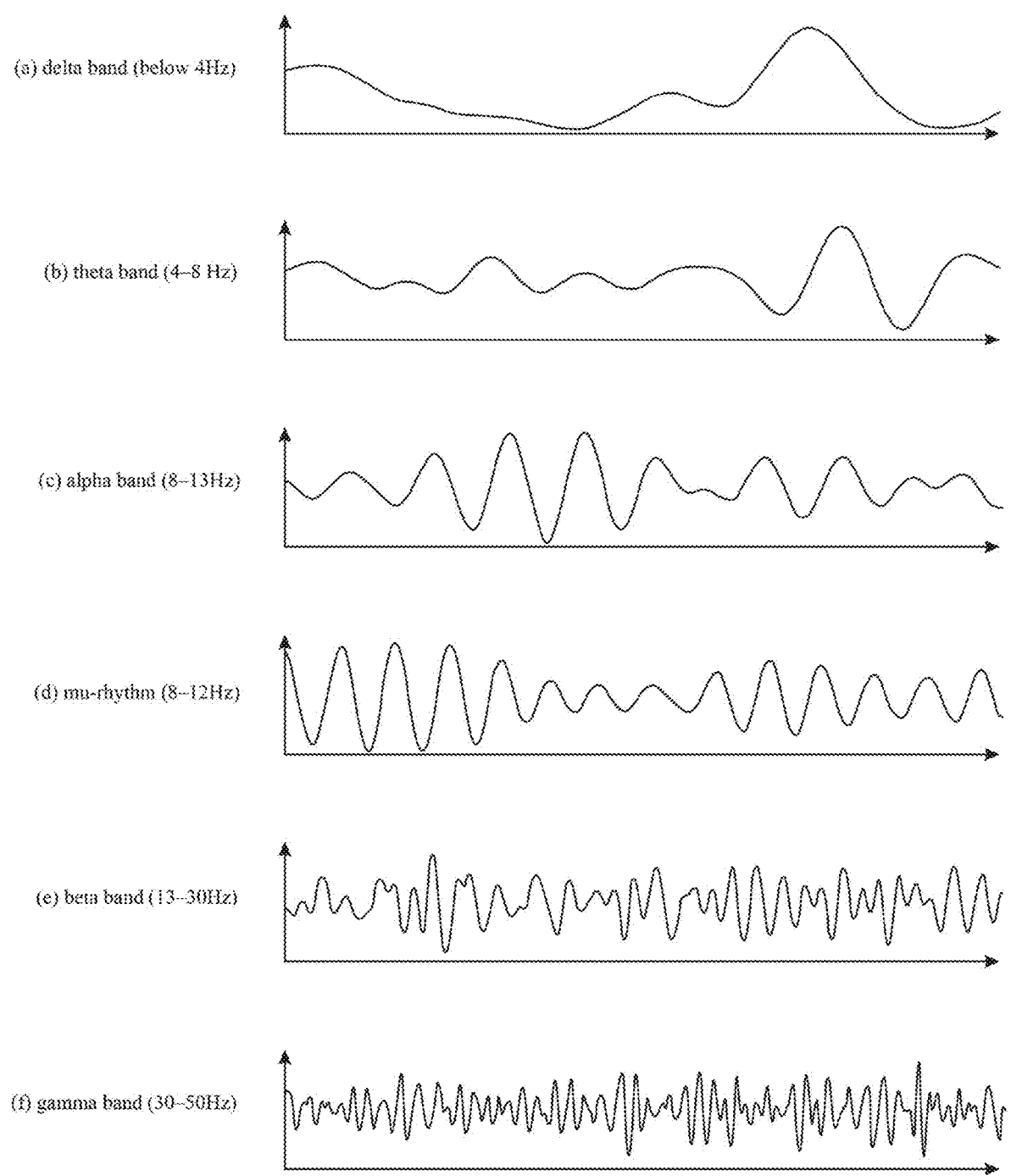
FIG. 18 is a graphical depiction of brainwaves from different frequency ranges.

In preferred embodiments of the systems and methodologies disclosed herein, one or more audio tracks or audio files may be provided that may be modulated, coordinated and/or synchronized with the operation of a plurality of LEDs or the light emitted therefrom. Preferably, the audio tracks or audio files include sound that is modulated, coordinated and/or synchronized with the LEDs or the light emitted therefrom at one or more frequencies selected from the ranges depicted in FIG. 18. The audio tracks or files (alone, or in combination with any light wavelengths utilized) may be selected to achieve a desired physiological or psychological effect in the user, either alone or in combination with the light therapy or brainwave entrainment.

The systems and methodologies disclosed herein may be utilized in conjunction with other methodologies or techniques. For example, these systems and methodologies may be used in combination with emotional freedom technique (EFT) tapping. EFT tapping is a holistic healing technique that may be utilized to treat various issues including, without limitation, stress, anxiety, phobias, emotional disorders, chronic pain, addiction, weight control, and limiting beliefs. EFT tapping involves tapping with the fingertips on specific meridian endpoints of the body, while focusing on negative emotions or physical sensations. Proponents of the method claim that it calms the nervous system, rewires the brain to respond in healthier ways, and restores the body's balance of energy.

One skilled in the art will further appreciate that the optimal parameters for a light therapy or brainwave entrainment session may depend on a variety of factors including, but not limited to, the condition being treated (or prevented), the physiological or psychological state of the user, the user's biometrics, and other such factors. In some use cases, selection of these parameters may be made by, or in coordination with, a physician, a psychiatrist, or other healthcare provider. These parameters may include, but are not limited to, the wavelengths of light to be utilized, the audio tracks or files to accompany the light therapy, the frequencies of oscillation utilized for the intensity in any of the wavelengths or light or sound, the portions of the user's head or body to be exposed to the light therapy, and the duration of the treatment.

While the devices and methodologies disclosed herein have frequently been described with reference to the use of traveling waves originating from a common source, one skilled in the art will appreciate that various embodiments of these methodologies and devices may also be produced which utilize waves originating from distinct sources (e.g., standing waves). In some embodiments, various devices, materials or other such measures may be taken to cause or prevent reflection of the waves used for light therapy or brainwave entrainment.

In accordance with the teachings herein, light therapy and/or PBMT may be administered to patients periodically or at various intervals, and may be administered in pre-operative or post-operative settings. Preferably, however, the light therapy and/or PBMT is applied as an adjuvant to, or proximal to, a surgical operation. Typically, the light therapy and/or PBMT will be applied within 8 hours of the surgery, preferably within 6 hours of the surgery, more preferably within 4 hours of the surgery, even more preferably within 2 hours of the surgery, and most preferably within 1 hour of the surgery. The frequency of the treatment may be varied based on various factors including, for example, the levels of certain biomarkers (such as, for example, the levels of one or more biomarkers selected from the group consisting of IL6, IL8, CCL3, CCL8, and CXCL6) observed in the patient (or in the patient's blood serum or CSF) at various points in time.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims. It will also be appreciated that the various features set forth in the claims may be presented in various combinations and sub-combinations in future claims without departing from the scope of the invention. In particular, the present disclosure expressly contemplates any such combination or sub-combination that is not known to the prior art, as if such combinations or sub-combinations were expressly written out.

What is claimed is:

1. A method for treating a subject, comprising: performing surgery on the subject; performing light therapy on the subject as an adjuvant to the surgery; determining a level of at least one biomarker, wherein said at least one biomarker is selected from a group consisting of cytokines and chemokines; and repeating the step of performing the light therapy if the level of the at least one biomarker is outside of a predetermined range.

2. The method of claim 1, wherein the surgery is selected from a group consisting of open heart surgery, heart valve replacement surgery and carotid endarterectomy.

3. The method of claim 1, wherein the light therapy is performed within 8 hours of the surgery.

4. The method of claim 1, wherein the light therapy is performed within 4 hours of the surgery.

5. The method of claim 1, wherein the light therapy is performed within 2 hours of the surgery.

6. The method of claim 1, wherein the light therapy is performed prior to the surgery.

7. The method of claim 1, wherein the light therapy is performed after the surgery.

8. The method of claim 1, further comprising repeating the step of performing the light therapy if the level of the at least one biomarker is above a predetermined threshold value.

9. The method of claim 1, further comprising:
determining levels $L_{i1}$ and $L_{i2}$ at corresponding times $t_{i1}$ and $t_{i2}$ of at least one biomarker $B_i$; and
repeating the step of performing the light therapy if $\Delta_i \geq k_i$, wherein $\Delta_i = |L_{i2} - L_{i1}|$, and wherein $k_i$ is a predetermined constant.

10. The method of claim 1, further comprising:
determining levels in the subject of a plurality of biomarkers $B_i \in [B_1, \ldots, B_n]$, wherein $n \geq 2$; and
repeating the step of performing the light therapy if any of the plurality of biomarkers $B_i$ has a level $|x_i|$ in excess of a corresponding threshold value $T_i$.

11. The method of claim 1, further comprising:
determining in the subject levels $L_{i1}$ and $L_{i2}$ at corresponding times $t_{i1}$ and $t_{i2}$ of a plurality of biomarkers $B_i \in [B_1, \ldots, B_n]$, wherein $n \geq 2$; and
repeating the step of performing the light therapy if, for at least one biomarker $B_i$, $\Delta_i \geq k_i$, wherein $\Delta_i = |L_{i2} - L_{i1}|$, and wherein $k_i$ is a predetermined constant.

12. The method of claim 1, further comprising:
determining in the subject levels $L_{i1}$ and $L_{i2}$ at corresponding times $t_{i1}$ and $t_{i2}$ of a plurality of biomarkers $B_i \in [B_1, \ldots, B_n]$, wherein $n \geq 2$; and
repeating the step of performing the light therapy if $P \geq k$, wherein P is the polynomial $P = \Sigma_1^n w_i \Delta_i$, wherein $\Delta_i = |L_{i2} - L_{i1}|$, $w_i$ is a weighting factor and wherein k is a predetermined constant.

13. The method of any of claim 12, wherein the at least one biomarker is selected from a group consisting of cytokines and chemokines.

14. The method of any of claim 12, wherein the at least one biomarker is selected from a group consisting of IL6, IL8, CCL3, CCL8 and CXCL6.

15. The method of any of claim 12, wherein the at least one biomarker is a cytokine selected from a group consisting of IL6 and IL8.

16. The method of any of claim 12, wherein the at least one biomarker is a chemokine selected from a group consisting of CCL3, CCL8 and CXCL6.

17. The method of claim 11, wherein the at least one biomarker includes IL6, wherein $k_{IL6} = 0$, and wherein $\Delta_{IL6}$ is measured at corresponding times (in hours post-surgery) $t_1 = 24$ and $t_2 = 32$.

18. The method of claim 11, wherein the at least one biomarker includes IL6, wherein $k_{IL8} = 0$, and wherein $\Delta_{IL8}$ is measured at corresponding times (in hours post-surgery) $t_1 = 24$ and $t_2 = 32$.

19. The method of claim 11, wherein the at least one biomarker includes IL6, wherein $k_{CCL3} = 0.1$, and wherein $\Delta_{CCL3}$ is measured at corresponding times (in hours post-surgery) $t_1 = 24$ and $t_2 = 32$.

20. The method of claim 11, wherein the at least one biomarker includes IL6, wherein $k_{CCL8} = 0$, and wherein $\Delta_{CCL8}$ is measured at corresponding times (in hours post-surgery) $t_1 = 24$ and $t_2 = 32$.

21. The method of claim 11, wherein the at least one biomarker includes IL6, wherein $k_{CXCL6} = 0$, and wherein $\Delta_{CXCL6}$ is measured at corresponding times (in hours post-surgery) $t_1 = 24$ and $t_2 = 32$.

22. The method of claim 1, wherein the light therapy includes PBMT.

23. The method of claim 1, wherein the light therapy is used in conjunction with binaural beats.

24. The method of claim 1, wherein the surgery is open heart surgery.

25. The method of claim 1, wherein the surgery is heart valve replacement surgery.

26. The method of claim 1, wherein the surgery is a carotid endarterectomy.

27. The method of claim 1, wherein the light therapy is performed using wavelengths selected from a group consisting of red and near-infrared wavelengths.

28. The method of claim 1, wherein the light therapy is performed using electromagnetic radiation having an oscillating polarization state.

29. The method of claim 1, wherein the light therapy is performed using electromagnetic radiation having oscillating and non-oscillating wavelengths.

30. The method of claim 1, wherein determining a level of at least one biomarker includes determining the level of the at least one biomarker in cerebral spinal fluid (CSF).

31. The method of claim 1, wherein determining a level of at least one biomarker includes determining the level of the at least one biomarker in blood serum.

32. A method for treating a subject, comprising:
performing a carotid endarterectomy on the subject;
performing photobiomodulation (PBM) on the subject as an adjuvant to the surgery using a PBM device, wherein the PBM device is equipped with an LED array which emits wavelengths selected from a group consisting of red and near-infrared wavelengths;
determining levels in the subject of a plurality of biomarkers $B_i \in [B_1, \ldots, B_n]$, wherein $n \geq 2$, and wherein each of the plurality of biomarkers is a cytokine; and
repeating the step of performing the light therapy if any of the plurality of biomarkers $B_i$ has a level $x_i$ outside of a predetermined range $R_i$.

33. The method of claim 32, further comprising:
modulating an intensity of at least one wavelength of light emitted by the LED array at a frequency within the range of 20 Hz to 60 Hz.

34. The method of claim 32, further comprising:
modulating an intensity of at least one wavelength of light emitted by the LED array at a frequency within the range of 30 Hz to 50 Hz.

35. The method of claim 32, wherein the PBM is performed using electromagnetic radiation having an oscillating polarization state.

36. The method of claim 32, wherein the PBM is performed using electromagnetic radiation having oscillating and non-oscillating wavelengths.

37. The method of claim 32, wherein the light therapy is performed within 8 hours of the carotid endarterectomy.

38. The method of claim 32, wherein the light therapy is performed within 4 hours of the carotid endarterectomy.

* * * * *